United States Patent [19]

Wenk et al.

[11] Patent Number: 4,863,942
[45] Date of Patent: Sep. 5, 1989

[54] NOVEL RESORCINOL ETHERS AND ANTI-INFLAMMATORY AND ANTI-ALLERGIC USE THEREOF

[75] Inventors: Paul Wenk, Allschwil; Alfred Sallmann, Bottmingen, both of Switzerland; Andreas Beck, Freiburg, Fed. Rep. of Germany

[73] Assignee: Ciba-Geigy Corporation, Hawthorne, N.Y.

[21] Appl. No.: 911,553

[22] Filed: Sep. 25, 1986

Related U.S. Application Data

[63] Continuation-in-part of Ser. No. 736,929, May 22, 1985, abandoned.

[30] Foreign Application Priority Data

May 24, 1984 [CH] Switzerland ........................ 2558/84
Feb. 15, 1985 [CH] Switzerland .......................... 702/85

[51] Int. Cl.$^4$ .................... A61K 31/41; A61K 31/165; C07D 257/04; C07C 125/00
[52] U.S. Cl. .................................... 514/381; 514/563; 548/253; 562/433
[58] Field of Search ................ 548/253; 514/381, 563; 562/433

[56] References Cited

U.S. PATENT DOCUMENTS 3,966,965 6/1976 Sellstedt et al. ................... 424/309
4,442,115 4/1984 Ramsden et al. .................. 548/253

FOREIGN PATENT DOCUMENTS 0028063 5/1981 European Pat. Off. .

Primary Examiner—David B. Springer
Attorney, Agent, or Firm—JoAnn Villamizar; Irving M. Fishman

[57] ABSTRACT

Novel 4-acylresorcinol ethers of the formula

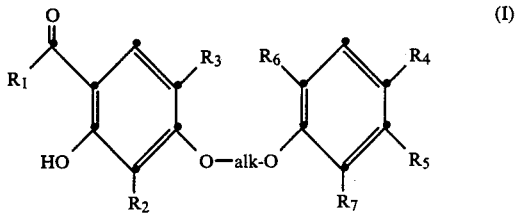

in which $R_1$ represents lower alkyl, $R_2$ represents lower alkyl, lower alkenyl or lower alkynyl, $R_3$ represents hydrogen, lower alkoxy, trifluoromethyl or halogen, alk represents an alkylene radical, one of the radicals $R_4$, $R_5$ and $R_7$ is a group of the formula —NH—C(=O)—$R_8$, a radical $R_4$ or $R_5$ that is other than a group of the formula —NH—C(=O)—$R_8$ is a radical $R_9$ and a radical $R_7$ that is other than a group of the formula —NH—C(=O)—$R_8$ is a radical $R_{10}$, $R_6$ represents hydrogen, lower alkyl, halogen, trifluoromethyl, optionally esterified or amidated carboxy, cyano or lower alkanoyl, $R_8$ represents optionally esterified or amidated carboxy, or 5-tetrazolyl, $R_9$ represents hydrogen, lower alkyl, lower alkoxy, halogen or trifluoromethyl, and $R_{10}$ represents hydrogen, lower alkyl, lower alkoxy, halogen, trifluoromethyl, cyano or optionally esterified or amidated carboxy, and their salts have LTD$_4$-antagonistic and PLA$_2$-phospholipase-inhibiting properties. They can be manufactured according to methods known per se.

35 Claims, No Drawings

NOVEL RESORCINOL ETHERS AND ANTI-INFLAMMATORY AND ANTI-ALLERGIC USE THEREOF

This is a Continuation-in-Part Application of our co-pending Patent Application Ser. No. 736,929, filed May 22, 1985, abandoned.

The invention relates to novel 4-acylresorcinol ethers of the formula

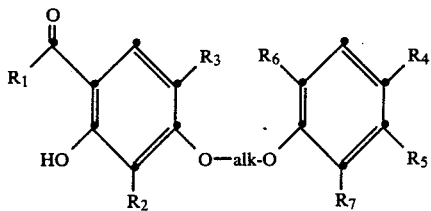

in which $R_1$ represents lower alkyl, $R_2$ represents lower alkyl, lower alkenyl or lower alkynyl, $R_3$ represents hydrogen, lower alkoxy, trifluoromethyl or halogen, alk represents an alkylene radical, one of the radicals $R_4$, $R_5$ and $R_7$ is a group of the formula —NH—C(=O)—$R_8$, a radical $R_4$ or $R_5$ that is other than a group of the formula —NH—C(=O)—$R_8$ is a radical $R_9$ and a radical $R_7$ that is other than a group of the formula —NH—C(=O)—$R_8$ is a radical $R_{10}$, $R_6$ represents hydrogen, lower alkyl, halogen, trifluoromethyl, optionally esterified or amidated carboxy, cyano or lower alkanoyl, $R_8$ represents optionally esterified or amidated carboxy, or 5-tetrazolyl, $R_9$ represents hydrogen, lower alkyl, lower alkoxy, halogen or trifluoromethyl, and $R_{10}$ represents hydrogen, lower alkyl, lower alkoxy, halogen, trifluoromethyl, cyano or optionally esterified or amidated carboxy, and to their salts.

The invention relates, for example, to compounds of the formula I, wherein either $R_4$ denotes a group $R_9$, $R_5$ denotes a group of the formula —NH—C(=O)—$R_8$ and $R_7$ denotes a group $R_{10}$, the radicals $R_1$, $R_2$, $R_3$, $R_6$, $R_8$, $R_9$ and $R_{10}$ having the meanings given hereinbefore, especially those, wherein $R_8$ is different from carboxy and lower alkoxycarbonyl, if $R_3$, $R_6$ and $R_9$ represent hydrogen and $R_{10}$ represents hydrogen, carboxy, lower alkoxycarbonyl, carbamoyl or cyano, or $R_4$ denotes a group of the formula —NH—C(=O)—$R_8$, $R_5$ denotes a group $R_9$, $R_7$ denotes a group $R_{10}$, the radicals $R_1$, $R_2$, $R_3$, $R_6$, $R_8$, $R_9$ and $R_{10}$ having the meanings given hereinbefore, especially those, wherein $R_8$ is different from 5-tetrazolyl, if $R_3$, $R_6$, $R_9$ and $R_{10}$ represent hydrogen, including their salts, especially their pharmaceutical acceptable salts.

Alkylene radicals alk may have up to and including 9 chain members and are, for example, straight-chain alkylene radicals of the formula

  (Ia)

in which m represents an integer of from 2 up to and including 9, but they may also be branched alkylene radicals, especially alkylene radicals that are branched in a position higher than the α-position or lower than the ω-position, and they are in each case preferably lower alkylene radicals of the type mentioned.

Esterified carboxy is, for example, lower alkoxycarbonyl but in the case of $R_8$ it may also be N,N-di-lower alkylamino-lower alkoxycarbonyl, N,N-lower alkyleneamino-lower alkoxycarbonyl, N,N-(aza)-lower alkyleneamino-lower alkoxycarbonyl that is optionally substituted, N,N-(oxa)-lower alkyleneamino-lower alkoxycarbonyl or N,N-(thia)-lower alkyleneamino-lower alkoxycarbonyl.

Amidated carboxy is, for example, carbamoyl, N-mono- or N,N-di-lower alkylcarbamoyl, also N,N-lower alkylene- or N,N-(aza)-lower alkylene-, N,N-(oxa)-lower alkylene- or N,N-(thia)-lower alkylene-carbamoyl, but in the case of $R_8$ it may also be N-(N',N'-di-lower alkylamino-lower alkyl)-carbamoyl, N-(N',N'-lower alkyleneamino-lower alkyl)-carbamoyl, or N-[N',N'-(aza)-lower alkyleneamino-lower alkyl]-carbamoyl that is optionally substituted, N-[N',N'-(oxa)-lower alkyleneamino-lower alkyl]-carbamoyl or N-[N',N'-(thia)-lower alkyleneamino-lower alkyl]-carbamoyl.

Hereinbefore and hereinafter, "lower" organic compounds and groups derived therefrom should be understood as being, for example, those having up to and including 7, especially up to and including 4, carbon atoms (C-atoms).

Lower alkyl is, for example, methyl, ethyl, propyl, isopropyl or butyl, also secondary or tertiary butyl.

Lower alkoxy is, for example, methoxy, ethoxy, propoxy, isopropoxy or butoxy.

Halogen has, for example, an atomic number of up to and including 53, especially of from 17 up to and including 53, and is, for example, fluorine, chlorine, bromine or iodine.

Lower alkenyl is, for example, allyl, also methallyl or but-4-enyl.

Lower alkynyl is, for example, propargyl.

Lower alkanoyl is, for example, formyl, acetyl, propionyl, butyryl, valeroyl or pivaloyl.

Straight-chain lower alkylene is, for example, ethylene, 1,3-propylene, 1,4-butylene, 1,5-pentylene, 1,6-hexylene or 1,7-heptylene but may also be 1,2-propylene, 1,3-butylene or 2,4-pentylene.

Branched lower alkylene is, for example, 1,3-(2-methyl)-propylene or 1,3-(2,2-dimethyl)-propylene.

Lower alkoxycarbonyl is, for example, methoxy-, ethoxy-, propoxy-, isopropoxy- or butoxy-carbonyl.

N,N-di-lower alkylamino-lower alkoxycarbonyl is, for example, 2-(dimethylamino)-ethoxycarbonyl, 2-(diethylamino)-ethoxycarbonyl or 3-(dimethylamino)-propoxycarbonyl.

N,N-lower alkyleneamino-lower alkoxycarbonyl is, for example, 2-(pyrrolidino)-, 2-(piperidino)- or 2-(tetrahydroazepino)-ethoxycarbonyl.

Optionally substituted N,N-(aza)-lower alkyleneamino-lower alkoxycarbonyl is, for example, 2-(piperazino)-ethoxycarbonyl, 2-(4-methylpiperazino)-ethoxycarbonyl or 2-(4-phenylpiperazino)-ethoxycarbonyl that is optionally substituted in the phenyl moiety by lower alkyl, lower alkoxy, halogen and/or by trifluoromethyl.

N,N-(Oxa)- or N,N-(thia)-lower alkyleneamino-lower alkoxycarbonyl is for example, 2-morpholino- or 2-thiomorpholinoethoxycarbonyl, N-mono- or N,N-di-lower alkylcarbamoyl is, for example, N-methyl-, N-ethyl- or N,N-dimethyl-carbamoyl.

N,N-lower alkylenecarbamoyl or N,N-(aza)-, N,N-(oxa)- or N,N-(thia)-lower alkylenecarbamoyl is, for example, pyrrolidino-, piperidino-, pyridazino-, (4-methyl)-piperazino-, morpholino- or thiomorpholino-carbonyl.

N-(N',N'-di-lower alkylamino-lower alkyl)-carbamoyl is, for example, N-[2-(N',N'-dimethylamino)-ethyl]- or N-[2-(N',N'-diethylamino)-ethyl]-carbamoyl.

N-(lower alkyleneamino-lower alkyl)-carbamoyl is, for example, N-[2-(pyrrolidino)-ethyl]- or N-[2-(piperidino)-ethyl]-carbamoyl.

Optionally substituted N-[N',N'-(aza)-lower alkyleneamino-lower alkyl]-carbamoyl is, for example, N-[2-(piperazino)-ethyl]-carbamoyl, N-[2-(4-methyl-piperazino)-ethyl]-carbamoyl or N-[2-(4-phenyl-piperazino)-ethyl]-carbamoyl that is optionally substituted in the phenyl moiety by lower alkyl, lower alkoxy, halogen and/or by trifluoromethyl.

N-[N',N'-(oxa)-lower alkyleneamino-lower alkyl]-carbamoyl is, for example, N-[2-(morpholino)-ethyl]-carbamoyl.

N-[N',N'-(thia)-lower alkyleneamino-lower alkyl]-carbamoyl is, for example, N-[2-(thiamorpholino)-ethyl]-carbamoyl.

Suitable salts of compounds of the formula I are preferably pharmaceutically acceptable salts, such as metal salts, ammonium salts or salts with organic bases. Metal salts are, for example, corresponding alkali metal and alkaline earth metal salts, for example lithium, sodium, potassium, magnesium or calcium salts, also pharmaceutically acceptable transition metal salts, such as zinc or copper salts. Salts with organic bases are formed, for example, from compounds of the formula I in which $R_6$ and/or $R_7$ represent(s) carboxy and/or $R_8$ represents carboxy or 5-tetrazolyl, with mono-, di- or tri-substituted organic amines, such as corresponding alkylamines, hydroxyalkylamines, suitable heterocycles having at least one N-atom, such as morpholine, thiomorpholine, piperidine or pyrrolidine, optionally N-substituted aminosaccharides, for example N-methyl-D-glucamine, or basic amino acids, such as lysine, arginine, histidine or ornithine, those having the L-configuration being preferred. There come into consideration as alkylamines, for example, mono-, di- or tri-lower alkylamines, such as ethyl-, tert.-butyl-, diethyl-, diisopropyl-, trimethyl- or triethyl-amine. Hydroxyalkylamines are, for example, mono-, di- or tri-hydroxyalkylamines, such as mono-, di- or tri-ethanolamine or diisopropanolamine, or hydroxy-lower alkyl-lower alkylamines, such as N,N-dimethyl- or N,N-diethyl-aminoethanol or tri-(hydroxymethyl)-methylamine.

Other salts that should be mentioned are pharmaceutically acceptable acid addition salts, such as hydrohalides, methanesulphonates, N-cyclohexylsulphamates, maleates, fumarates, malates or tartrates of compounds of the formula I in which the radical $R_8$ is capable of forming corresponding salts.

The compounds of the formula I having chiral carbon atoms may, depending on the number of those chiral carbon atoms, be in the form of enantiomers or diastereoisomers or they may be in the form of mixtures of the same, for example diastereoisomeric mixtures, racemates or racemic mixtures.

The novel compounds are distinguished by valuable pharmacological properties.

For example, they have an anti-allergic action which is based on a pronounced $LTD_4$ (leucotriene-$D_4$) and PAF (PAF-acetoether) antagonism. The $LTD_4$-antagonistic properties of the compounds according to the invention can be demonstrated, for example, in vitro by their inhibitory action on $LTD_4$-induced contractions of the isolated ileum of guinea-pigs, which action can be detected at concentrations of from approximately 0.03 to approximately 0.10 $\mu mol/l$, and in vivo by their inhibitory action on $LTD_4$-induced bronchospasms in guinea-pigs, which action can be detected, in the case of intravenous treatment, at doses of approximately 0.08 mg/kg and above and, in the case of aerosol treatment, at an active ingredient content of approximately 0.025% by weight and above.

Anti-allergically active compounds of similar structure are already known. For example, in U.S. Patent Specification No. 4,448,728, compounds of the formula I in which $R_1$ and $R_2$ represent $C_1-C_6$-alkyl, $R_5$ represents a group of the formula $-NH-C(=O)-R_8$ in which $R_8$ represents carboxy or $C_1-C_6$-alkoxycarbonyl, $R_3$, $R_4$ and $R_6$ represent hydrogen, $R_7$ represents hydrogen, cyano, carboxy or $C_1-C_6$-alkoxycarbonyl and alk represents a group of the formula $-(CH_2)_m-$ (Ia), in which m represents an integer in the range of from 2 to 6, or a group of the formula $-(CH_2)_n-CH_2-CH(OH)-CH_2-(CH_2)_n$ in which one of the indices n represents 0, 1, 2, 3 or 4 and the other represents 0 or 1, are proposed as anti-allergic agents.

The compounds according to the invention are superior to those compounds in that they have a more prolonged action, and they possess, in addition to the mentioned $LTD_4$-antagonistic action, phospholipaseinhibiting properties that are novel to this class of compound and a pronounced anti-inflammatory or skin-phlogistic action which is very valuable in itself and also supplements the anti-allergic action in a desirable manner. The phospholipase-inhibiting properties can be demonstrated, for example, in vitro by the inhibition, detectable at concentrations of approximately 10 $\mu mol/l$ and above, of the activity of phospholipases $A_2$ (obtained from human leucocytes) and C (obtained from human thrombocytes), and the anti-inflammatory or skin-phlogistic properties can be demonstrated, for example, in vivo by the inhibitory action on the experimental croton oil ear oedema in rats at concentrations of approximately 10 mg/ml and above.

The compounds according to the invention can accordingly be used as anti-allergic agents, for example for the treatment of asthma, hay fever, rhinitis and skin allergies, but especially as anti-inflammatory agents and more especially for the treatment of inflammatory diseases of the rheumatic type, and also as skin and mucosa phlogistics, for the treatment of inflammatory dermatoses having various causes, but especially allergic causes, for example for the treatment of inflammatory skin irritations, contact dermatitis, exanthemas, burns and mucosa inflammations of the eyes, lips, mouth and the genital and anal regions.

The inhibitory action on the experimental ear oedema in rats can be effected according to the method of G. Tonelli and L. Thibault described in Endocrinology 77, 625 (1965). In this model, for example an inhibiting concentration $IC_{50}$ of 15 mg/ml was ascertained for N-{3-[3-(4-acetyl-3-hydroxy-2-n-propyl-phenoxy)-propoxy]-2-cyanophenyl}-1H-tetrazole-5-carboxamide. To ascertain the other properties mentioned, there may be used, for example, the following test procedures.

Inhibitory action on $LTD_4$-induced contractions of the guinea-pig ileum

Contractions, the severity of which is recorded, are induced by synthetic $LTD_4$ (leucotriene-$D_4$, potassium salt) in ileum segments that have been taken from guinea-pigs having a body weight of from 300 to 400 g, fastened in an organ bath in Tyrode's solution (38° C., gassing with 95% $O_2$ and 5% $CO_2$) and charged with lp. The degree of inhibition of these contractions that is attributable to the LTD$_4$-antagonistic action of the test substance is measured. The concentration of test substance that reduces LTD$_4$-induced contractions to 50% of the starting value is ascertained, this concentration being termed IC$_{50}$. In this test procedure, for example an IC$_{50}$ value of 0.015 μmol/l was obtained for the triethanol-ammonium salt of N-{3-[3-(4-acetyl-3-hydroxy-2-propyl-phenoxy)-propoxy]-6-methyl-phenyl}-oxamic acid and an IC$_{50}$ value of 0.008 μmol/l was obtained for the triethanolammonium salt of N-{3-[3-(4-acetyl-3-hydroxy-2-propyl-phenoxy)-propoxy]-4-bromo-6-methylphenyl}-1H-tetrazole-5-carboxamide.

Bronchoconstriction test in guinea-pigs (in vivo, intravenous)

Male guinea-pigs weighing from 400 to 700 g are anaesthetised intraperitoneally with 1.4 g/kg of urethane and there is introduced into the jugular vein a polyethylene tube through which active ingredients can be administered intravenously. A second polyethylene tube is introduced into the trachea. The pressure in the oesophagus is measured by means of a tube which is introduced into the oesophagus and which is connected to a Statham pressuretransducer. The animal is placed in a plexiglass chamber which can be closed in an airtight manner and which is connected to a Fleisch tube No. 000 and a Validyne transducer MP 45-1. The flow is measured by means of this arrangement.

After the surgical preparation of the experimental animals a certain time is allowed to elapse so that the pulmonary functions can stabilise. The compound to be tested is then administered in accordance with the following protocol.

At the beginning of the test, LTD$_4$ (300 ng/kg i.v.) is administered to the experimental animals. 10 minutes later LTD$_4$ (300 ng/kg i.v.) is administered for the second time. After a further 10 minutes, the test substance is injected intravenously 1 minute before the third administration of LTD$_4$ (300 ng/kg i.v.).

The reduction in the compliance caused by the second LTD$_4$ administration (control) is compared with the reduction in the compliance caused by the third LTD$_4$ administration. The inhibition of the compliance in the first minute after the administration of LTD$_4$ is calculated from the average value of three animals by means of the following formula:

$$\% \text{ inhibition} = 100 - \frac{(100 - \text{compliance preparation}) \times 100}{(100 - \text{compliance control})}$$

If different doses of active ingredient are investigated, then the percentage inhibition for each individual dose is recorded by entering the log of the dose on the abscissa against the percentage inhibition on the ordinate. The IC$_{50}$ is then ascertained by linear regression analysis.

Bronchoconstriction test in guinea-pigs (in vivo, aerosol)

Male guinea-pigs weighing from 400 to 700 g are anaesthetised intraperitoneally with 1.4 g/kg of urethane, and a polyethylene tube is introduced into the jugular vein. A second polyethylene tube is introduced into the trachea. The pressure in the oesophagus is recorded by means of a tube which is introduced into the oesophagus and which is connected to a Statham pressure transducer. The animal is placed in a plexiglass chamber which can be closed in an airtight manner and which is connected to a Fleisch tube No. 000 and a Validyne transducer MP 45-1. The flow is measured by means of this arrangement.

After the surgical preparation of the experimental animals a certain time is allowed to elapse so that the pulmonary functions can stabilise. The compound to be tested is then administered in accordance with the following protocol. The experimental animals are exposed for one minute to a 1% aerosol solution of the compound to be tested (weight/volume) or to distilled water (for control purposes). A Monaghan ultrasound spray device (model 670) whose particle size ranges from 1 to 8 microns, the majority being 3 microns, is used for all test compounds administered by inhalation.

Aqueous solutions are each freshly prepared and introduced by means of an on-stream drug vial into the chamber of the spray device. The spray produced is administered to the experimental animals via a 65 ml glass chamber which is connected by a tube to the trachea. At the end of the treatment period, LTD$_4$ (0.3 μg/ml) is administered for 2 minutes by means of a second Monaghan ultrasound spray device (model 670) and via a glass chamber of the type mentioned above. The reduction in the compliance in the third minute after the administration of LTD$_4$ is read by comparing the average value of three animals with the average value of three control animals and the percentage inhibition of the compliance is calculated in accordance with the following formula:

$$\% \text{ inhibition} = 100 - \frac{(100 - \text{compliance preparation}) \times 100}{(100 - \text{compliance control})}$$

If different concentrations of active ingredient are investigated, then the percentage inhibition for each concentration is recorded by entering the log concentration on the abscissa against the percentage inhibition on the ordinate. The IC$_{50}$ is then ascertained by linear regression analysis.

In the last-mentioned test procedure, for example an IC$_{50}$ value of 0.024% of the aerosol solution was ascertained for the triethanolammnnium salt of N-{3-[3-(4-acetyl-3-hydroxy-2-n-propyl-phencx,y)-propoxy]-6-methyl phenyl}-oxamic acid and an IC$_{50}$ value of 0.033% of the aerosol solution was ascertained for the triethanolammonium salt of N-{3-[3-(4-acetyl-3-hydroxy-2-n-propyl-phenoxy)-propoxy]-4-bromo-6-methyl}-oxamic acid.

In vitro test for determining the inhibition of phospholipase A$_2$ obtained from human leucocytes Human neutrophilic polymorphonuclear leucocytes are isolated from "buffy coats" by multistage fractional sedimentation and deep-frozen. Phospholipase A$_2$ is extracted from the cell suspension by homogenisation with the addition of ice-cold 0.36N $H_2SO_4$ in 2M NaCl and the supernatant obtained after centrifugation at 10,000 g is dialysed against sodium acetate buffer pH 4.5.

In order to determine the enzyme activity, enzyme (10–30 μg protein) is incubated for one hour at 37° in 0.1M tris/HCl buffer pH 7 with the addition of 1 mM CaCl$_2$ and substrate consisting of phospholipids (2 μM) of *Escherichia coli* that have been radioactively labelled with $^{14}$C-oleic acid by means of biosynthesis. The reaction is stopped by the addition of Dole reagent (isopropanol/heptane/1N $H_2SO_4$ 40:10:1, v/v) and the $^{14}C$-oleic acid released selectively by phospholipase $A_2$ is extracted. Substrate that is extracted at the same time is completely removed by filtering the extract through a column of silica gel. The $^{14}C$-oleic acid in the eluate is determined radiometrically.

In order to ascertain the inhibitory action of test substances on phospholipase $A_2$, these substances are added to the incubation mixture in the form of solutions in water, dimethyl sulphoxide (final concentration in the mixture up to 5% by volume) or ethanol (final concentration in the mixture up to 2.5% by volume). The strength of action of the test substances is expressed by the $IC_{50}$, that is to say the concentration that brings about a 50% inhibition of the control activity The $IC_{50}$ is ascertained on a graph by entering the percentage inhibition on the ordinate against the logarithm of the concentration ($\mu M$) on the abscissa.

In this model the following values were obtained for the $IC_{50}$ in $\mu mol/l$:
the triethanolammonium salt of N-{3-[3-(4-acetyl-3-hydroxy-2-n-propyl-phenoxy)-propoxy]-2-cyanophenyl}-oxamic acid: 30;
the triethanolammonium salt of N-{3-[3-(4-acetyl-3-hydroxy-2-n-propyl-phenoxy)-propoxy]-phenyl}-oxamic acid: 23;
the triethanolammonium salt of N-{3-[3-(4-acetyl-3-hydroxy-2-n-propyl-phenoxy)-propoxy]-4-bromo-6-methylphenyl}-oxamic acid: 15;
the triethanolammonium salt of N-{3-[3-(4-acetyl-3-hydroxy-2-n-propyl-phenoxy)-propoxy]-4-bromo-6-methylphenyl}-1H-tetrazole-5-carboxamide: 10;
the triethanolammonium salt of N-{3-[3-(4-acetyl-3-hydroxy-2-n-propyl-phenoxy)-propoxy]-2-cyanophenyl}-1H-tetrazole-5-carboxamide: 20;
the sodium salt of N-{3-[3-(4-acetyl-3-hydroxy-2-n-propyl-phenoxy)-2-hydroxypropoxy]-2-cyanophenyl}-oxamic acid: inactive at 100;
the sodium salt of N-{3-[3-(4-acetyl-3-hydroxy-2-n-propyl-phenoxy)-2-hydroxypropoxy]-phenyl}-oxamic acid: inactive at 100.

Under the test conditions described, mepacrine inhibits phospholipase $A_2$ with an $IC_{50}$ of 1600 $\mu mol/l$.

In vitro test for determining the inhibition of phospholipase C obtained from human thrombocytes Human thrombocytes are obtained from "buffy coats" by fractional centrifugation and then deep-frozen. Phospholipase C is released by ultrasound treatment of the cell suspension and, after ultracentrifugation (150,000 g, 1 hour) is in soluble form in the supernatant.

In order to determine the enzyme activity, enzyme (20–100 $\mu g$ protein) is incubated for 5 minutes at 37° in 0.025M tris/malate buffer pH 6 with the addition of 0.2 mM $CaCl_2$ and 0.02 mM radioactively labelled substrate, phosphatidyl- [$^{14}C$]-inositol. The reaction is stopped by extraction by shaking with $CHCl_3/CH_3OH$ 2:1 (v/v). Substrate that has not been consumed is extracted into the organic phase while the reaction product, $^{14}C$-inositol phosphate, remains in the aqueous phase and can be measured by radiometry of an aliquot.

In order to ascertain the inhibitory action of test substances on phospholipase C, these substances are added to the incubation mixture in the form of solutions in water or dimethyl sulphoxide (final concentration in the mixture up to 5% by volume). The strength of action of the test substances is expressed by the $IC_{50}$, that is to say the concentration that brings about a 50% inhibition of the control activity. The $IC_{50}$ is ascertained on a graph by entering the percentage inhibition on the ordinate against the logarithm of the concentration ($\mu M$) on the abscissa.

In this model, the following values were obtained for the $IC_{50}$ in $\mu mol/l$:
the triethanolammonium salt of N-{3-[3-(4-acetyl-3-hydroxy-2-n-propyl-phenoxy)-propoxy]-2-cyanophenyl}-1H-tetrazole-5-carboxamide: 14;
the sodium salt of N-{3-[3-(4-acetyl-3-hydroxy-2-n-propyl-phenoxy)-2-hydroxypropoxy]-2-cyanophenyl}-oxamic acid: inactive at 100.

Under the test conditions described, mepacrine inhibits phospholipase C with an $IC_{50}$ of 20 $\mu M$.

The invention relates especially to compounds of the formula I in which $R_1$ represents lower alkyl, $R_2$ represents lower alkyl, lower alkenyl or lower alkynyl, $R_3$ represents hydrogen, lower alkoxy, trifluoromethyl or halogen, alk represents lower alkylene, one of the radicals $R_4$, $R_5$ and $R_7$ is a group of the formula —C(C=O)—$R_8$, a radical $R_4$ or $R_5$ that is other than a group of the formula —C(C=O)—$R_8$ is a radical $R_9$ and a radical $R_7$ that is other than a group of the formula —C(C=O)—$R_8$ is a radical $R_{10}$, $R_6$ represents hydrogen, lower alkyl, halogen, lower alkanoyl, carboxy, lower alkoxycarbonyl, carbamoyl, N-mono- or N,N-di-lower alkylcarbamoyl, N,N-lower alkylene- or N,N-(aza)-lower alkylene-, N,N-(oxa)-lower alkylene- or N,N-(thia)-lower alkylene-carbamoyl, $R_8$ on the one hand represents carboxy, lower alkoxycarbonyl, N,N-di-lower alkylamino-lower alkoxycarbonyl, N,N-lower alkyleneamino-lower alkoxycarbonyl, N,N-(aza)-lower alkyleneamino-lower alkoxycarbonyl that is optionally substituted the lower alkyl, or by phenyl which may itself be substituted by lower alkyl, lower alkoxy, halogen and/or by trifluoromethyl, N,N-(oxa)-lower alkyleneamino-lower alkoxycarbonyl or N,N-(thia)-lower alkyleneamino-lower alkoxycarbonyl, carbamoyl, N-mono- or N,N-di-lower alkylcarbamoyl, N,N-lower alkylene- or N,N-(aza)-lower alkylene-, N,N-(oxa)-lower alkylene- or N,N-(thia)-lower alkylene-carbamoyl, N-(N',N'-di-lower alkylamino-lower alkyl)-carbamoyl, N-(N',N'-lower alkyleneamino-lower alkyl)-carbamoyl, N-[N',N'-(aza)-lower alkyleneamino-lower alkyl]-carbamoyl that is optionally N''-substituted by lower alkyl, or by phenyl which may itself be substituted by lower alkyl, lower alkoxy, halogen and/or by trifluoromethyl, N-[N',N'-(oxa)-lower alkyleneamino-lower alkyl]-carbamoyl or N-[N',N'-(thia)-lower alkyleneamino-lower alkyl]-carbamoyl, and $R_8$ on the other hand represents 5-tetrazolyl, $R_9$ represents hydrogen, lower alkyl, lower alkoxy, halogen or trifluoroxethyl, and $R_{10}$ represents hydrogen, lower alkyl, lower alkoxy, halogen, trifluoromethyl, carboxy, lower alkoxycarbonyl, cyano, carbamoyl, N-mono- or N,N-di-lower alkylcarbamoyl, N,N-lower alkylene- or N,N-(aza)-lower alkylene-, N,N-(oxa)-lower alkylene- or N,N-(thia)-lower alkylene-carbamoyl, and to their salts, especially pharmaceutically acceptable salts.

The invention relates more especially to compounds of the formula I in which $R_1$ represents lower alkyl having up to and including 4 carbon atoms, such as methyl, $R_2$ represents lower alkyl having up to and including 4 carbon atoms, such as propyl, $R_3$ represents hydrogen, one of the radicals $R_4$ and $R_5$ is a group of the formula —NH—C(=O)—$R_8$ and the other is a radical $R_9$, $R_6$ represents hydrogen, lower alkyl having up to and including 4 carbon atoms, such as methyl, halogen having an atomic number of up to and including 35, such as fluorine, chlorine or bromine, cyano, lower alkoxycarbonyl having up to and including 5 carbon atoms, such as ethoxycarbonyl, carboxy, or lower alkanoyl having up to and including 7 carbon atoms, such as formyl, acetyl or pivaloyl, $R_7$ represents hydrogen, lower alkyl having up to and including 4 carbon atoms, such as methyl, lower alkoxy having up to and including 4 carbon atoms, such as methoxy, or halogen having an atomic number of up to and including 35, such as chlorine or bromine, $R_8$ on the one hand represents carboxy, lower alkoxycarbonyl having up to and including 4 carbon atoms, such as methoxy- or ethoxycarbonyl, di-lower alkylamino-lower alkoxycarbonyl having up to and including 4 carbon atoms in the di-lower alkylamino moiety and also in the lower alkoxy moiety, such as 2-(dimethylamino)-ethoxycarbonyl, carbamoyl, N-mono- or N,N-di-lower alkylcarbamoyl in which lower alkyl has up to and including 4 carbon atoms, such as N-methyl-, N-ethyl- or N,N-dimethylcarbamoyl, or N-(N',N'-di-lower alkylamino-lower alkyl)-carbamoyl having up to and including 4 carbon atoms in the di-lower alkylamino moiety and also in the lower alkyl moiety, such as N-[(2-dimethylamino)-ethyl]-carbamoyl, and $R_8$ on the other hand represents 5-tetrazolyl, $R_9$ represents hydrogen, lower alkyl having up to and including 4 carbon atoms, such as methyl, halogen having an atomic number of from 17 up to and including 53, such as chlorine, bromine or iodine, or trifluoromethyl, and alk represents, especially, straight-chain, terminally bonded lower alkylene having up to and including 7 carbon atoms, such as 1,3-propylene or 1,5-pentylene, especially those, wherein $R_4$ is different from 5-tetrazolylcarbonylamino, if $R_3$, $R_5$, $R_6$ and $R_7$ represent hydrogen and to their salts, especially pharmaceutically acceptable salts.

The invention relates more especially, for example, to compounds of the formulae

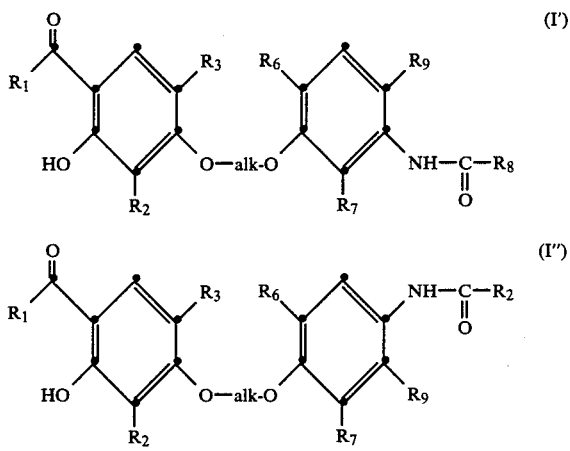

in which in formula I' $R_1$ represents lower alkyl having up to and including 4 carbon atoms, such as methyl, $R_2$ represents lower alkyl having up to and including 4 carbon atoms, such as propyl, $R_3$ represents hydrogen, $R_6$ represents hydrogen, lower alkyl having up to and including 4 carbon atoms, such as methyl, halogen having an atomic number of up to and including 35, such as chlorine or bromine, lower alkoxycarbonyl having up to and including 5 carbon atoms, such as ethoxycarbonyl, cyano, carboxy, or lower alkanoyl having up to and including 7 carbon atoms, such as formyl, acetyl or pivaloyl, $R_7$ represents hydrogen, lower alkyl having up to and including 4 carbon atoms, such as methyl, lower alkoxy having up to and including 4 carbon atoms, such as methoxy, or halogen having an atomic number of up to and including 35, such as chlorine or bromine, $R_8$ on the one hand represents carboxy, lower alkoxycarbonyl having up to and including 4 carbon atoms, such as methoxy- or ethoxycarbonyl, di-lower alkylamino-lower alkoxycarbonyl having up to and including 4 carbon atoms in the di-lower alkylamino moiety and also in the lower alkoxy moiety, such as 2-(dimethylamino)-ethoxycarbonyl, carbamoyl, N-mono- or N,N-di-lower alkylcarbamoyl in which lower alkyl has up to and including 4 carbon atoms, such as N-methyl-, N-ethyl- or N,N-dimethylcarbamoyl, N-(N',N'-di-lower alkylamino-lower alkyl)-carbamoyl having up to and including 4 carbon atoms in the di-lower alkylamino moiety and also in the lower alkyl moiety, such as N-[(2-dimethylamino)-ethyl]-carbamoyl, and $R_8$ on the other hand represents 5-tetrazolyl, $R_9$ represents hydrogen, lower alkyl having up to and including 4 carbon atoms, such as methyl, halogen having an atomic number of from 17 up to and including 53, such as chlorine, bromine or iodine, or trifluoromethyl, and alk represents, especially, straight-chain, terminally bonded lower alkylene having up to and including 4 carbon atoms, such as 1,3-propylene or 1,3-(2-hydroxy)-propylene, or in which in formula I" $R_1$ represents lower alkyl having up to and including 4 carbon atoms, such as methyl, $R_2$ represents lower alkyl having up to and including 4 carbon atoms, such as propyl, $R_6$ represents hydrogen, lower alkyl having up to and including 4 carbon atoms, such as methyl, halogen having an atomic number of up to and including 35, such as chlorine or bromine, lower alkoxycarbonyl having up to and including 5 carbon atoms, such as ethoxycarbonyl, carboxy, or lower alkanoyl having up to and including 7 carbon atoms, such as formyl, acetyl, or pivaloyl, $R_7$ represents hydrogen, lower alkyl having up to and including 4 carbon atoms, such as methyl, lower alkoxy having up to and including 4 carbon atoms, such as methoxy, or halogen having an atomic number of up to and including 35, such as chlorine or bromine, $R_8$ on the one hand represents carboxy, lower alkoxycarbonyl having up to and including 4 carbon atoms, such as methoxy- or ethoxy-carbonyl, di-lower alkylamino-lower alkoxycarbonyl having up to and including 4 carbon atoms in the di-lower alkylamino moiety and also in the lower alkoxy moiety, such as 2-(dimethylamino)-ethoxycarbonyl, carbamoyl, N-mono- or N,N-di-lower alkylcarbamoyl in which lower alkyl has up to and including 4 carbon atoms, such as N-methyl-, N-ethyl- or N,N-dimethyl-carbamoyl, N-(N',N'-di-lower alkylamino-lower alkyl)-carbamoyl having up to and including 4 carbon atoms in the di-lower alkylamino moiety and also in the lower alkyl moiety, such as N-[(2-dimethylamino)-ethyl]-carbamoyl, and $R_8$ on the other hand represents 5-tetrazolyl and alk represents, especially, straight-chain, terminally bonded lower alkylene having up to and including 4 carbon atoms, such as 1,3-propylene or 1,3-(2-hydroxy)-propylene, especially those in which $R_8$ is different from 5-tetrazolyl, if $R_3$, $R_6$, $R_9$ and $R_{10}$ represent hydrogen, and in either case to their salts, especially pharmaceutically acceptable salts.

Within the above-mentioned group of compounds, the invention relates more especially to compounds according to the formula I' in which $R_1$ represents lower alkyl having up to and including 4 carbon atoms, $R_2$ represents straight-chain lower alkyl having up to and including 4 carbon atoms, $R_3$ represents hydrogen, $R_6$ represents hydrogen, lower alkyl having up to and including 4 carbon atoms, such as methyl, halogen having an atomic number of up to and including 35, such as fluorine, chlorine or bromine, lower alkoxycarbonyl having up to and including 5 carbon atoms, such as methoxycarbonyl, cyano or carboxy, $R_7$ represents hydrogen or lower alkyl having up to and including 4 carbon atoms or halogen having an atomic number of up to and including 35, such as chlorine, $R_8$ represents carboxy or 5-tetrazolyl, and alk represents straight-chain, terminally bonded lower alkylene having up to and including 4 carbon atoms, such as 1,3-propylene, and to their salts, especially pharmaceutically acceptable salts, with bases.

The invention relates preferably to compounds of the formula I in which $R_1$ represents lower alkyl having up to and including 4 carbon atoms, such as methyl, $R_2$ represents straight-chain lower alkyl having up to and including 4 carbon atoms, such as propyl, $R_3$ represents hydrogen, $R_4$ represents hydrogen, lower alkyl, such as methyl, trifluoromethyl, or halogen having an atomic number of up to and including 35, such as chlorine or bromine, $R_5$ represents oxaloamino or 5-tetrazolylcarbonylamino, $R_6$ represents hydrogen, lower alkyl having up to and including 4 carbon atoms, such as methyl, halogen having an atomic number of up to and including 35, such as chlorine or bromine, lower alkoxycarbonyl having up to and including 5 carbon atoms, such as ethoxycarbonyl, or carboxy, $R_7$ represents hydrogen, lower alkyl having up to and including 4 carbon atoms, such as methyl, halogen having an atomic number of up to and including 35, such as chlorine, carboxy, lower alkoxycarbonyl having up to and including 5 carbon atoms, such as methoxycarbonyl, carbamoyl or cyano, and alk represents straight-chain, terminally bonded lower alkylene having up to and including 4 carbon atoms, such as 1,3-propylene, and to their salts, especially pharmaceutically acceptable salts, with bases.

The invention relates especially to compounds of the formula I in which $R_1$ represents lower alkyl having up to and including 4 carbon atoms, such as methyl, $R_2$ represents straight-chain lower alkyl having up to and including 4 carbon atoms, such as propyl, $R_3$ represents hydrogen, $R_4$ represents hydrogen, lower alkyl, such as methyl, trifluoromethyl, or halogen having an atomic number of up to and including 35, such as chlorine or bromine, $R_5$ represents oxaloamino or 5-tetrazolylcarbonylamino, $R_6$ represents hydrogen, lower alkyl having up to and including 4 carbon atoms, such as methyl, halogen having an atomic number of up to and including 35, such as chlorine or bromine, lower alkoxycarbonyl having up to and including 5 carbon atoms, such as ethoxycarbonyl, or carboxy, $R_7$ represents hydrogen, lower alkyl having up to and including 4 carbon atoms, such as methyl, or halogen having an atomic number of up to and including 35, such as chlorine or bromine, and alk represents straight-chain, terminally bonded lower alkylene having up to and including 4 carbon atoms, such as 1,3-propylene, and to their salts, especially pharmaceutically acceptable salts, with bases.

The invention relates more especially to compounds of the formula I in which $R_1$ represents lower alkyl having up to and including 4 carbon atoms, such as methyl, $R_2$ represents straight-chain lower alkyl having up to and including 4 carbon atoms, such as propyl, $R_3$ and $R_7$ represent hydrogen, one of the radicals $R_4$ and $R_6$ represents lower alkyl having up to and including 4 carbon atoms, such as methyl, and the other represents halogen having an atomic number of up to and including 35, such as fluorine, chlorine or bromine, $R_5$ represents oxaloamino or 5-tetrazolylcarbonylamino, and alk represents straight-chain, terminally bonded lower alkylene having up to and including 7 carbon atoms, such as 1,3-propylene, and to their salts, especially pharmaceutically acceptable salts, with bases.

The invention relates more especially, for example, to compounds according to the formula I' in which $R_1$ represents lower alkyl having up to and including 4 carbon atoms, such as methyl, $R_8$ represents carboxy or 5-tetrazolyl, $R_2$ represents straight-chain lower alkyl having from 2 up to and including 4 carbon atoms, such as propyl, $R_3$ represents hydrogen, $R_9$ represents hydrogen and $R_6$ and $R_7$ each represents, independently of the other, hydrogen or lower alkyl having up to and including 4 carbon atoms, such as methyl, or $R_9$ represents lower alkyl having up to and including 4 carbon atoms, such as methyl, or trifluoromethyl, $R_7$ represents hydrogen, and $R_6$ represents hydrogen, or halogen having an atomic number of up to and including 35, such as chlorine, fluorine or bromine, or $R_9$, $R_6$ and $R_7$ represent the same or different halogen atoms having an atomic number of up to and including 35, such as chlorine, and alk represents straight-chain, terminally bonded lower alkylene having from 2 up to and including 4 carbon atoms, such as 1,3-propylene, and to their salts, especially pharmaceutically acceptable salts, with bases.

The invention relates very especially to compounds of the formula I in which $R_1$ represents lower alkyl having up to and including 4 carbon atoms, such as methyl, $R_2$ represents straight-chain lower alkyl having from 2 up to and including 4 carbon atoms, such as propyl, $R_3$ represents hydrogen, and $R_5$ represents oxaloamino or 5-tetrazolylcarbonylamino, and in which $R_4$ represents hydrogen and $R_6$ and $R_7$ each represents, independently of the other, hydrogen or lower alkyl having up to and including 4 carbon atoms, or $R_4$ represents lower alkyl having up to and including 4 carbon atoms, such as methyl, or trifluoromethyl, $R_6$ represents hydrogen or halogen having an atomic number of up to and including 35, such as chlorine or bromine, and $R_7$ represents hydrogen, or $R_4$, $R_6$ and $R_7$ represent the same or different halogen atoms having an atomic number of up to and including 35, such as chlorine or bromine, and alk represents straight-chain, terminally bonded lower alkylene having from 2 up to and including 4 carbon atoms, such as 1,3-propylene, and to their salts, especially pharmaceutically acceptable salts, with bases.

The invention relates specifically to the compounds of the formula I mentioned in the Examples and to their salts, especially pharmaceutically acceptable salts, with bases.

The invention also relates to a process for the manufacture of compounds of the formula I and their salts that is based on methods known per se. This process is characterised in that a) in a compound of the formula

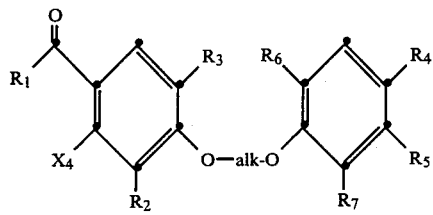

(VI)

in which $X_4$ represents a radical that can be converted into hydroxy, $X_4$ is converted into hydroxy, or b) there are reacted with one another compounds of the formulae

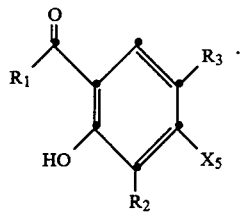

(VII)

and

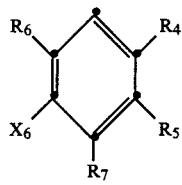

(VIII)

in which one of the radicals $X_5$ and $X_6$ is hydroxy that is optionally in salt form and the other is a radical —O—alkH that is substituted by reactive esterified hydroxy, that is to say an alkoxy radical that is substituted by reactive esterified hydroxy, or c) a compound of the formula

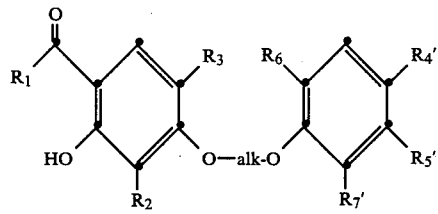

(X)

in which one of the radicals $R_4'$, $R_5'$ and $R_7'$ is an amino group, a radical $R_4'$ or $R_5'$ that is other than an amino group is a radical $R_9$ and a radical $R_7'$ that is other than an amino group is a radical $R_{10}$, or a salt thereof, is reacted with a compound of the formula $$X_7-R_{8'}$$ (XI)

in which $R_{8'}$ represents an optionally esterified or amidated carboxy group, or 5-tetrazolyl that is optionally protected in the 1-position, and $X_7$ represents an optionally esterified, amidated or anhydridised carboxy group or, if $R_{8'}$ represents 5-tetrazolyl that is protected in the 1-position, $X_7$ represents a carboxy group that is optionally in salt form, and any protecting group in the 1-position of a tetrazolyl group $R_8$ is removed, or (d) in a compound of the formula

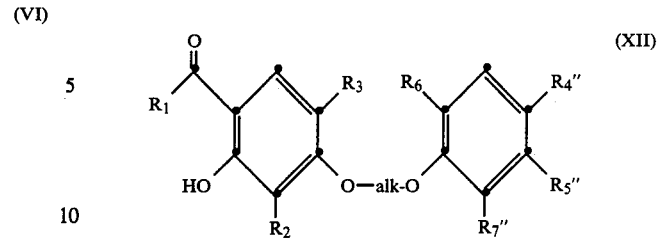

(XII)

in which one of the radicals $R_4''$, $R_5''$ and $R_7''$ is a radical $X_8$, a radical $R_4''$ or $R_5''$ that is other than a radical $X_8$ is a radical $R_9$ and a radical $R_7''$ that is other than a radical $X_8$ is a radical $R_{10}$, and $X_8$ represents a radical that can be converted into the desired group of the formula —NH—C(=O)—$R_8$, $X_8$ is converted into that group, and, if desired, a compound obtainable according to the process is converted into a different compound of the formula I, an isomeric mixture obtainable according to the process is separated and the desired isomer(s) is(are) isolated, and/or a free compound obtainable according to the process is converted into a salt or a salt obtainable according to the process is converted into the free compound or into a different salt.

Radicals $X_4$ in the formula VI that can be converted into hydroxy are, for example, etherified or esterified hydroxy groups There come into consideration as etherified hydroxy $X_4$, for example, aliphatically etherified hydroxy, for example lower alkoxy, such as methoxy, or lower alkenyloxy, especially lower alk-2-enyloxy, for example allyloxy, phenyl-lower alkoxy, especially optionally substituted phenyl-lower alkoxy, such as benzyloxy, also tetrahydropyran-2-yloxy or silyloxy, especially tri-lower alkylsilyloxy, for example trimethylsilyloxy. Esterified hydroxy $X_4$ is, for example, hydroxy esterified by a carboxylic acid, such as an aliphatic or aromatic carboxylic acid, or by an aliphatic or aromatic semiester of carbonic acid, such as lower alkanoyloxy, for example acetoxy, optionally substituted benzoyloxy, for example of the formula $R_1$—C(=O)—O—, optionally halogenated lower alkoxycarbonyl, for example methoxy-, ethoxy- or tert.-butoxycarbonyl, 2,2,2-triiodoethoxy- or 2,2,2-trichloroethoxycarbonyl, optionally substituted phenyl-lower alkoxycarbonyl, especially 1-phenyl-lower alkoxycarbonyl, for example benzyloxycarbonyl, or optionally substituted phenoxycarbonyl.

Salt-form hydroxy $X_5$ in formula VII, salt-form hydroxy $X_6$ in formula VIII and salt-form carboxy in formula XI are especially alkali metal salts, for example sodium or potassium salts.

Alkoxy radicals $X_5$ in formula VII and alkoxy radicals $X_6$ in formula VIII that are substituted by reactive esterified hydroxy are, for example, alkoxy radicals that are substituted by reactive esterified hydroxy, for example reactive esterified hydroxyalkoxy radicals, especially of the formula —O—(CH$_2$)$_m$—X in which X represents reactive esterified hydroxy and m represents an integer of from 2 up to and including 9. Reactive esterified hydroxy is, for example, halogen, such as chlorine, bromine or iodine, or organic sulphonyloxy, such as lower alkanesulphonyloxy, for example methanesulphonyloxy, or optionally substituted benzenesulphonyloxy, for example benzene-, p-bromobenzene- or p-toluene-sulphonyloxy.

Optionally esterified, amidated or anhydridised carboxy $X_7$ in formula XI is, for example, free carboxy, esterified carboxy $R_8$, carboxy esterified by an optionally substituted phenol, such as phenoxy-, 4-nitrophenoxy- or 2,4-dinitrophenoxy-carbonyl, amidated carboxy $R_8$ or activated carbamoyl, such as 1-imidazolyl- or 1-(2,5-dimethylimidazolyl)-carbonyl, or carboxy anhydridised by a hydrohalic acid, such as halocarbonyl, for example of the formula Hal—C(=O)— in which Hal represents chlorine, bromine or iodine, especially chlorine.

There come into consideration as starting materials XI especially those of the formula $R_8''$—$R_8''$ (XIa) in which $R_8''$ represents optionally esterified or amidated carboxy, or those of the formula Hal—C(=O)—$R_8'$ (XIb'). 5-tetrazolyl radicals $R_8'$ that are in protected form are, for example, 1-(α-aralkyl)-tetrazol-5-yl radicals that are optionally substituted in the aryl moiety, such as 1-benzyltetrazol-5-yl or 1-(p-methoxybenzyl)-tetrazol-5-yl.

A radical $X_8$ in formula XII that can be converted into a group of the formula —NH—C(=O)—$R_8$ is, for example, a radical that can be converted into that group by solvolysis, that is to say hydrolysis, alcoholysis (reaction with the alcohol corresponding to the desired esterified carboxy group $R_8$) and/or aminolysis (reaction with ammonia or an amine corresponding to the desired amidated carboxy group $R_8$), for example a group of the formula —NH—$X_A$ in which $X_A$ represents a functionally modified oxalo group that is other than an optionally esterified or amidated oxalo group and that can be converted into that group. Functionally modified oxalo groups of this type are preferably those that have, as functionally modified α-carbonyl grouping, thioxomethylene, iminomethylene or an esterified and/or etherified dihydroxymethylene grouping, and/or, as functionally modified carboxy group, a functionally modified carboxy group that is other than an esterified or amidated carboxy group. Esterified and/or etherified dihydroxymethylene groupings are, for example, dihydroxymethylene groups that are esterified by a hydrohalic acid, such as hydrochloric acid, and/or etherified by a lower alkanol, such as methanol or ethanol. There may be mentioned as examples especially dihalomethylene groupings, such as dichloromethylene, lower alkoxyhalomethylene groupings, such as methoxy- or ethoxy-chloromethylene, or di-lower alkoxymethylene groupings, such as dimethoxy- or diethoxy-methylene. Functionally modified carboxy groupings other than esterified or amidated carboxy groups are, for example, the cyano group, anhydridised carboxy groups, such as halocarbonyl, for example chlorocarbonyl, imino ester groupings, such as imide or amine halide groupings, for example iminochloro- or aminodichloro-methyl, imino alether groupings, such as lower alkyl- or lower alkyleneimino ether groupings, for example methoxy- or ethoxyiminomethylene, 4,4- or 5,5-dimethyloxazolin-2-yl or 4,4,6-trimethyldihydrooxazolin-2-yl, amidino groups, such as amidino or lower alkylamidino, for example methylamidino, ortho acid groupings esterified by a hydrohalic acid, such as hydrochloric acid, and/or etherified by a lower alkanol, such as tri-lower alkoxy-, lower alkoxyhalo- or trihalo-methyl groups, especially trimethoxy- or triethoxy-methyl, ethoxy- dichloromethyl or trichloromethyl, or optionally esterified thiocarboxy groups, such as lower alkylthiocarbonyl groups, for example ethylthiocarbonyl.

A radical that can be converted into a group of the formula —NH—C(=O)—$R_8$ in which $R_8$ represents 5-tetrazolyl is, for example, a group of the formula —NH—C(=O)—CN or a group of the formula —NH—C(=O)—$R_8'$ in which $R_8'$ is 5-tetrazolyl that is protected in the 1-position. 5-tetrazolyl radicals $R_8'$ that are in protected form are, for example, 1-(α-aralkyl)-tetrazol-5-yl radicals that are optionally substituted in the aryl moiety, such as 1-benzyltetrazol-5-yl or 1-(p-methoxybenzyl)-tetrazol-5-yl.

Other radicals $X_8$ that can be converted into groups of the formula —NH—C(=O)—$R_8$ are, for example, groups of the formula —NH—$X_B$ which can be converted by oxidation into those groups and in which $X_B$ represents an optionally hydrated glyoxyl group that can be converted by oxidation into the oxalo group of the formula —C(=O)—$R_8$ in which $R_8$ represents carboxy. This glyoxyl group can advantageously be formed in situ in the course of the oxidation reaction, for example from the acyl group of an optionally α,β-unsaturated or α,β-dihydroxylated aliphatic or araliphatic carboxylic acid, from a glycoloyl group that is optionally esterified at the hydroxy group or from a glycyl group, or it can advantageously be freed from one of its functional derivatives, for example one of its acetals or imines. Acyl groups of optionally α,β-unsaturated or α,β-dihydroxylated carboxylic acids are, for example, alkanoyl groups, such as lower alkanoyl, for example acetyl, acyl groups of α,β-unsaturated aliphatic mono- or di-carboxylic acids are, for example, acryloyl, crotonyl or the acyl group of optionally functionally modified fumaric or maleic acid, acyl groups of α,β-unsaturated araliphatic carboxylic acids are, for example, optionally substituted cinnamoyl, or acyl groups of aliphatic α,β-dihydroxydicarboxylic acids, such as tartaric acid, or monofunctional carboxy derivatives, such as esters or amides, thereof Esterified glycoloyl groups are, for example, glycoloyl groups that are esterified at the hydroxy group by a mineral acid, such as a hydrohalic acid, for example hydrochloric or hydrobromic acid, or by a carboxylic acid, for example acetic acid or optionally substituted benzoic acid. Acetalised glyoxyloyl groups are, for example, glyoxyloyl groups that are acetalised by lower alkanols or a lower alkanediol, such as dimethoxy-, diethoxy- or ethylenedioxy-acetyl. Imines of glyoxyloyl groups are, for example, optionally substituted N-benzylimines or N-(2-benzothiazolyl)-imines thereof or imines with 3,4-di-tert.-butyl-o-quinone. Other radicals that can be converted by oxidation into the oxalo group are, for example, optionally substituted 2-furoyl groups, such as 2-furoyl groups having an acetalised formyl group, such as diethoxymethyl, in the 5-position. Groups that can be oxidised to form esterified oxalo groups of the formula —C(=O)—$R_8$ in which $R_8$ represents esterified carboxy are etherified glycoloyl groups, such as lower alkoxyacetyl. Radicals $X_B$ that can be oxidised to form optionally esterified or amidated oxaloamino groups are also optionally hydrated or acetalised formylmethylamino groups or optionally functionally modified carboxymethylamino or carboxymethyleneimino groups, for example of the formula —NH—CH$_2$—CH=O, —NH—CH$_2$—$R_8$ or —N=CH—$R_8$.

The carrying out of the reactions according to the process and the manufacture of novel starting materials and intermediates are effected analogously to the methods used for the reaction and formation of known starting materials and intermediates. Even when not expressly mentioned below, the customary auxiliaries, such as catalysts, condensation agents and solvolysis agents and/or solvents or diluents, and the customary reaction conditions, such as temperature and pressure conditions, and, optionally, the customary protective gases, are used.

The conversion of groups $X_4$ into hydroxy according to process variant a) is carried out in customary manner, for example by treatment with a complex metal halide of the formula $M^nY_n$ (XIX) in which M represents an n-valent, co-ordinatively unsaturated metal cation of group IIa, IIb, IIIa, IIIb, IVb, Va or VIIIb of the Periodic Table of Elements, for example the magnesium, zinc(II), boron(III), aluminium(III), gallium(III), tin-(IV), titanium(IV), antimony(V) or iron(III) or iron(VI) ion, and Y represents a halogen atom having an atomic number of up to and including 35, such as fluorine or chlorine, for example aluminium trichloride, or by treatment with a tertiary organic ammonium salt, such as a pyridinium or tri-lower alkylammonium halide, for example pyridinium chloride or bromide or triethylammonium chloride, but it can also be carried out by solvolysis, especially hydrolysis, if necessary in the presence of a hydrolysis agent that is preferably acidic. In addition to customary basic hydrolysis agents, such as alkali metal hydroxides, hydrolysis agents are, as acidic hydrolysis agents, for example, mineral acids, for example hydrochloric, hydrobromic or hydriodic acid, sulphuric acid, phosphoric acid or polyphosphoric acid, also complex metal acids, for example hexachloroantimonic acid, tetrafluoroboric acid and the like, and, in the case of hydroxy groups $X_4$ esterified by organic carboxylic acids, also lower alkanoic acids, such as acetic acid. Solvents used in the case of hydrolysis are, for example, water-miscible organic solvents. The operation is preferably carried out in each case in the presence of a solvent or diluent or a solubiliser, while cooling or heating, for example in a temperature range of approximately from 0° to 120° C., and/or udder an inert gas.

Thus, etherified hydroxy groups can be cleaved to form hydroxy, for example, by treatment with aqueous hydriodic acid, pyridinium hydrochloride, for example in methylene chloride, with hydrobromic acid in highly concentrated, for example 98%, acetic acid, or by treatment with boron tribromide or aluminium trichloride. In a modification of this process, a compound of the formula VI in which $X_4$ represents lower alk-2-enyloxy and $R_2$ represents hydrogen can be rearranged to form a compound of the formula I in which $R_2$ is lower alk-2-enyl by heating to approximately from 150° to 250° C., preferably to approximately from 190° to 220° C., advantageously in a solvent, such as diphenyl ether or N,N-dimethyl- or N,N-diethylaniline.

In compounds VI having as the group $X_4$ an optionally substituted α-phenyl-lower alkoxy group or another customary protected hydroxy group that can be cleaved by reduction, the hydroxy group can advantageously be freed by reduction. For example, it is possible to hydrogenate, that is to say reduce with hydrogen in the presence of a hydrogenation catalyst, for example a palladium, platinum, nickel or rhodium catalyst, for example palladium-on-carbon or Raney nickel.

In addition, starting from compounds VI in which $X_4$ is hydroxy esterified by an organic carboxylic acid, the hydroxy group can be freed by transesterification, that is to say by treatment with an alcohol, for example a lower alkanol, in the presence of an acidic or basic agent, such as a mineral acid, for example sulphuric acid, or an alkali metal hydroxide or alcoholate, for example sodium hydroxide or a sodium lower alkoxide.

Starting materials VI are manufactured, for example, as follows: there are reacted with one another compounds of the formulae

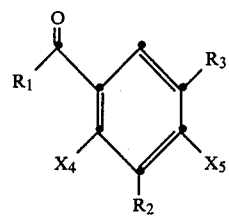 (XVIII)

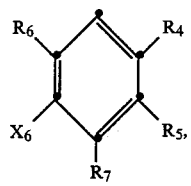 (VIII)

in which one of the radicals $X_5$ and $X_6$ is hydroxy that is optionally in salt form and the other is a radical —O—alkH that is substituted by reactive esterified hydroxy, for example a group of the formula —O—(CH$_2$)$_m$—X in which X represents reactive esterified hydroxy, for example halogen.

The reaction of compounds VII and VIII according to process variant b) is carried out in customary manner, for example in the presence of a basic condensation agent, such as a hydroxide or carbonate of an alkali or alkaline earth metal, such as sodium or potassium hydroxide, potassium carbonate or calcium carbonate, advantageously in a lower alkanol, for example methanol or amyl alcohol, a di-lower alkyl ketone, for example acetone or diethyl ketone, or an N,N-di-lower alkyl-lower alkanoic acid amide or an N-lower alkyl-lower alkanoic acid lactam, for example dimethylformamide or N-methylpyrrolidone.

The starting materials VII are manufactured, for example, as follows: a compound of the formula

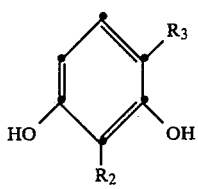 (XIII)

is reacted in the presence of a Lewis acid, for example aluminium trichloride or zinc chloride, with a compound of the formula $R_1$—$X_2$ [IV; $X_2$=halocarbonyl or —O—C(=O)—$R_1$] and, if desired, in the resulting compound VII in which $X_5$ represents hydroxy, the hydroxy group in the p-position with respect to $R_1$—C(=O)— is converted by reaction with a dihaloalkane, epoxyalkane or haoalkanol into an alkoxy radical that is substituted by halogen or hydroxy, and hydroxyalkoxy is reactively esterified, for example by treatment with thionyl chloride, phosphorus tribromide or a sulphonic acid chloride Compounds VIII can be obtained, for example, as follows: in a compound of the formula

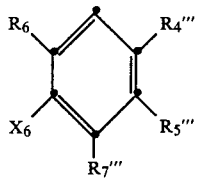

(XX)

in which one of the radicals R$_4'''$, R$_5'''$ and R$_7'''$ is a nitro group, a radical R$_4'''$ or R$_5'''$ that is other than a nitro group is a radical R$_9$ and a radical R$_7'''$ that is other than a nitro group is a radical R$_{10}$, the nitro group is reduced to form amino, for example using hydrogen in the presence of Raney nickel, and the compound of the formula

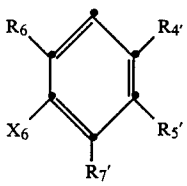

(XXI)

in which one of the radicals R$_4'$, R$_5'$ and R$_7'$ is an amino group, a radical R$_4'$ or R$_5'$ that is other than an amino group is a radical R$_9$ and a radical R$_7'$ that is other than an amino group is a radical R$_{10}$, is reacted in the presence of a base, for example triethylamine or pyridine, with a compound of the formula Hal—C(=O)—R$_8$ (XIb; Hal=halogen), and, if desired, in the resulting compound VIII in which X$_6$ represents hydroxy, the hydroxy group is converted into a halo- or hydroxy-substituted alkoxy radical by reaction with a dihaloalkane, epoxyalkane or haloalkanol, and hydroxyalkoxy is reactively esterified, for example by treatment with thionyl chloride, phosphorus tribromide or a sulphonic acid chloride.

The reaction of compounds X and XI according to process variant (c) can be carried out in customary manner, especially in the manner known from the literature for analogous reactions, if necessary in the presence of a condensation agent, for example, in the case of reaction with an ester halide or amide halide of oxalic acid, in the presence of a basic condensation agent, such as a tertiary organic nitrogen base, for example triethylamine or pyridine, or an alkali metal hydroxide or carbonate, for example sodium or potassium hydroxide, or, for example, in the case of reaction with oxalic acid, in the presence of a condensation agent that effects the dehydration of the ammonium salt that is formed initially, such as a water-binding agent, for example dicyclohexyl carbodiimide, or an isonitrile, such as tert.-butylisonitrile, or a mineral acid, for example hydrochloric acid, or an acid anhydride, for example phosphorus pentoxide, in each case in an inert solvent, such as a haloalkane, for example in methylene chloride, or an N,N-dialkylamide, for example N,N-dimethyl-formamide or -acetamide.

The protecting group in the 1-position of 5-tetrazolyl radicals R$_8'$ can then be removed, for example by acidolysis, that is to say treatment with an acid, for example trifluoroacetic acid/anisole, or by hydrogenolysis, especially by means of hydrogen and palladium-on-carbon.

Starting materials X can be manufactured, for example, as follows there are reacted with one another compounds of the formulae

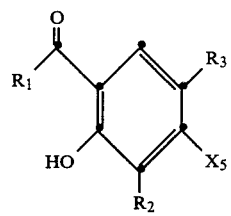

(VII)

and

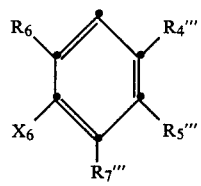

(XX)

in which one of the radicals R$_4'''$, R$_5'''$ and R$_7'''$ is a nitro group, a radical R$_4'''$ or R$_5'''$ that is other than a nitro group is a radical R$_9$ and a radical R$_7'''$ that is other than a nitro group is a radical R$_{10}$, and in which one of the radicals X$_5$ and X$_6$ is hydroxy that is optionally in salt form and the other is a radical —O—alkH that is substituted by reactive esterified hydroxy, for example a group of the formula —O—(CH$_2$)$_m$—X in which X represents reactive esterified hydroxy, for example halogen, and X', and in the resulting compound of the formula

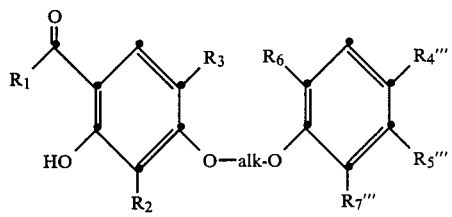

the nitro group is reduced to form amino, for example by reaction with hydrogen in the presence of a hydrogenation catalyst, such as palladium-on-carbon or, especially, Raney nickel, for example in tetrahydrofuran.

The conversion of the group X$_8$ in compounds XII into a group of the formula —NH—C(=O)—R$_8$ according to process variant (d) is carried out, for example, by solvolysis or oxidation or, when starting from groups X$_8$ of the formula NH—C(=O)—CN, by reaction with hydrazoic acid, or, when starting from groups X$_8$ of the formula —NHC(=O)—R$_8'$ in which R$_8'$ represents 5-tetrazolyl that is protected in the 1-position, by removing the protecting group. For example, the mentioned group X$_A$ in a radical X$_8$ of the formula —NH—X$_A$ can be converted by hydrolysis into the oxalo group. A group X$_A$ having as functionally modified carboxy group an imino ether, ortho ester or ester halide gropuing and/or, as functionally modified α-carbonyl group, thioxo- or imino-methylene or an esterified or etherified dihydroxymethylene group can also be hydrolysed to form an esterified oxalo group —C(-=O)—R$_8$. Likewise, a group X$_A$ having as functionally modified carboxy group a cyano group, an amidino grouping or an imide or amide halide grouping and/or, as functionally modified o-carbonyl group, thioxo- or imino-methylene or an etherified or esterified dihydroxymethylene group can be hydrolysed to form an amidated oxalo group —C(=O)—R$_8$. The hydrolysis can be carried out in customary manner, if necessary in the presence of a basic or, preferably, acidic hydrolysis agent, such as an alkali metal hydroxide, such as sodium or potassium hydroxide, or, preferably, a protonic acid, preferably a mineral acid, for example, a hydrohalic acid, such as hydrochloric acid, or an organic carboxylic or sulphonic acid, for example acetic acid or p-toluenesulphonic acid.

Functionally modified oxalo groups X$_A$ having as functionally modified carboxy group an anhydridised carboxy group, such as halocarbonyl, for example chlorocarbonyl, cyanocarbonyl, or a lower alkyleneimino ether grouping, for example 4,4- or 5,5-dimethyloxazolin-2-yl, or 4,4,6-trimethyldihydrooxazolin-2-yl, can also be converted by customary alcoholysis, that is to say reaction with the corresponding alcohol, into esterified oxalo groups —C(=O)—R$_8$. The alcoholysis of anhydridised carboxy groups is advantageously carried out in the presence of a basic condensation agent, for example pyridine or triethylamine, while the alcoholysis of carboxy or a lower alkyleneimino ether grouping is preferably carried out under acidic conditions, for example in the presence of hydrochloric acid, p-toluenesulphonic acid or acetic acid. Analogously, a functionally modified oxalo group having an anhydridised carboxy group can also be converted into an amidated oxalo group —C(=O)—R$_8$ by ammonolysis or aminolysis, that is to say reaction with ammonia or a corresponding primary or secondary amine, preferably in the presence of a basic condensation agent, for example sodium hydroxide, pyridine or triethylamine.

The conversion of the mentioned groups X$_B$ into those of the formula —NH—C(=O)—R$_8$ is carried out, for example, by oxidation. The oxidation can be carried out in customary manner by reaction with a suitable oxidising agent. Suitable oxidising agents are especially oxidising heavy metal compounds, such as silver compounds, for example silver nitrate or silver picolinate, oxy-acids of heavy metals, for example manganese(IV), manganese(VII), chromium(VI) and iron(III), or of halogens, or their anhydrides or salts, such as chromic acid, chromium dioxide, potassium dichromate, potassium permanganate, manganese dioxide, potassium hexacyanoferrate, sodium chlorite in the presence of sulphamic acid, sodium hypochlorite in the presence of nickel chloride, or sodium iodate, sodium eriodate or lead tetraacetate. The reaction with these oxidising agents is carried out in customary manner, for example in an inert solvent, such as acetone, acetic acid, pyridine or water, or an inert solvent mixture that is preferably aqueous, at normal temperature or, if necessary, while cooling or heating, for example at from approximately 0° C. to approximately 100° C. The oxidation of optionally etherified glycoloyl groups to form optionally esterified oxalo groups is carried out, for example, advantageously with potassium permanganate in aqueous pyridine or acetone at room temperature. Acetalised glyoxyl groups and iminoacetyl groups are preferably oxidised under acidic conditions, for example with potassium dichromate in sulphuric acid, acyl groups of α,β-dihydroxylated aliphatic carboxylic acids, such as the acyl radical of tartaric acid, are advantageously oxidised with periodic acid, while for the oxidation of the glycyl group there is preferably used potassium ferrate in alkaline medium, for example at pH 10-13, for example 11.5, or organic silver salts, such as silver picolinate. Groups of the formula —N=CH—R$_8$ are preferably oxidised by an organic peracid, for example peracetic acid or m-chloroperbenzoic acid, in an inert solvent, for example methylene chloride, chloroform or benzene..

The reaction of groups X$_8$ of the formula —NH—C(=O)—CN with hydrazoic acid is preferably carried out while forming the hydrazoic acid in situ by treating an alkali metal azide with an acid, such as hydrochloric acid, preferably in toluene or similar solvents.

The removal of the protecting group from groups X$_8$ of the formula —NH—C(=O)—R$_8'$ in which R$_8'$ represents 5-tetrazolyl that is protected in the 1-position is carried out in the manner customary for the protecting group in the 1-position, especially by acidolysis, that is to say treatment with an acid, for example with trifluoroacetic acid in an ether, such as anisole, or by catalytic hydrogenation, for example in the presence of palladium.

The starting materials XII are manufactured, for example, as follows: a compound of the formula

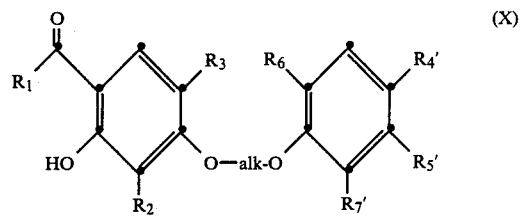

in which one of the radicals R$_4'$, R$_5'$ and R$_7'$ is an amino group, a radical R$_4'$ or R$_5'$ that is other than an amino group is a radical R$_9$ and a radical R$_7'$ that is other than an amino group is a radical R$_{10}$, or an acid addition salt thereof, is reacted with a corresponding acid, for example of the formula X$_A$—OH (XXVIIa) or X$_B$—OH (XXVIIb) or R$_8'$—COOH (XXVIIc) or a functional derivative thereof. Functional derivatives of acids XXVIIa to XXVIIc are especially acid derivatives containing an esterified, amidated or anhydridised carboxy group, such as lower alkoxycarbonyl, optionally substituted carbamoyl, for example carbamoyl or imidazolyl-1-carbonyl, or halocarbonyl, for example chloro- or bromo-carbonyl, or a group of the formula —CON$_3$ or —CON$_2\oplus$ Hal$\ominus$. As examples of acids XXVIIa and XXVIIb and their functional derivatives there may be mentioned especially: as functional derivatives of acids XXVIIa, oxalyl halides, such as oxalyl chloride or oxalyl bromide, tri-lower alkoxy- and dihalo-lower alkoxyacetic acid lower alkyl esters, such as oxalic acid tetraethyl ester or dichlorooxalic acid diethyl ester, oxalic acid imino dialkyl esters, such as oxalic acid mono- or di-imino diethyl ester, oxalic acid amidines, such as N-lower alkyloxalic acid ester amidines, oxalic acid dithio-lower alkyl esters, such as the dimethyl ester, cyanoformyl chloride or cyanogen, and, as acids XXVIIb and their functional derivatives, glycolic acids and their lower alkyl esters or the corresponding lactide, mono- or di-lower alkoxyacetic acid lower alkyl esters, such as ethyl esters, for example ethoxy- or diethoxy-acetic acid ethyl ester, haloacetic anhydrides, such as chloroacetic anhydride or chloroacetyl chloride and tartaric acid, or 2,3-diacetoxysuccinic acid anhydride, also cinnamoyl chloride, acetyl chloride and glycine. Functional derivatives of acids XXVIIc are especially chlorides thereof The reaction of compounds X and XXVIIa to XXVIIc or their derivatives can be carried out in customary manner, for example in the presence of a water-binding agent, such as an acid anhydride, for example phosphorus pentoxide, or dicyclohexyl carbodiimide, or a condensation agent that is, for example, acidic or basic, such as a mineral acid, for example hydrochloric acid, or an alkali metal hydroxide or carbonate, for example sodium or potassium hydroxide, or an organic nitrogen base, for example triethylamine or pyridine In the case of reaction with an acid anhydride, such as an acid chloride, an organic nitrogen base is preferably used as condensation agent. The reaction with carboxylic acids is preferably carried out in the presence of a water-binding agent. If necessary, the operation is carried out in an inert solvent, at normal temperature or while cooling or heating, for example in a temperature range of from approximately 0° to approximately 100° C., in a closed vessel and/or under an inert gas, for example nitrogen.

Analogously, compounds XII in which $X_8$ represents a group $R_8$—CH=N— can be manufactured by condensing compounds X with optionally esterified or amidated glyoxylic acid.

Compounds XII in which $X_8$ represents a group —NH—$X_B$ and $X_B$ represents glyoxyloyl can also be manufactured by heating a corresponding haloacetyl compound, such as a bromoacetyl compound, with hexamethylenetetramine, preferably in an aqueous alcohol, or by oxidising it with silver tetrafluoroborate in dimethyl sulphoxide. Similarly, it is also possible to oxidise a chloroacetyl compound with potassium dichromate in hexamethylphosphoric acid triamide in the presence of dicyclohexyl-18-crown-6-ether. Compounds XII in which $X_8$ represents a group —NH—$X_B$ and $X_B$ represents an iminoacetyl group, for example optionally substituted benzyliminoacetyl, can be manufactured starting from the corresponding glycyl compounds by reacting these with the corresponding carbonyl compound, for example with benzaldehyde, and rearranging the resulting intermediate, for example an N-benzylideneglycyl compound, preferably under the reaction conditions.

Functionally modified oxalo groups having an imino ether grouping as functionally mcdified carboxy group can be manufactured starting from the corresponding cyanocarbonyl compound by reaction with the corresponding alcohol, for example lower alkan(di)ol or amino-lower alkanol.

A compound of the general formula I obtainable according to the invention can be converted in a manner known per se into a different compound of the general formula I.

For example, a free carboxy group $R_6$, $R_7$ and/or $R_8$ can be reacted in customary manner, for example by treatment with a diazo-lower alkane or a tri-lower alkyloxonium, tri-lower alkylcarboxonium or di-lower alkylcarbonium salt, such as the hexachloroantimonate or hexafluorophosphate, or especially by reaction with the corresponding alcohol, for example a lower alkanol, N,N-di-lower alkylamino-lower alkanol, N,N-lower alkyleneamino-lower alkanol, N,N-(aza)-lower alkyleneamino-lower alkanol that is optionally substituted, N,N-(oxa)-lower alkyleneamino-lower alkanol or N,N-(thia)-lower alkyleneamino-lower alkanol, or a reactive derivative, such as a carboxylic, phosphorous, sulphurous or carbonic acid ester, thereof, for example a corresponding lower alkanecarboxylic acid ester, tri-lower alkyl phosphite or di-lower alkyl sulphite, to form compounds of the general formula I in which $R_6$, $R_7$ and/or $R_8$ represent esterified carboxy. The reaction with the corresponding alcohol itself can advantageously be carried out in the presence of an acidic catalyst, such as a protonic acid, for example hydrochloric, hydrobromic, sulphuric, phosphoric, boric, benzenesulphonic and/or toluenesulphonic acid, in an inert solvent, especially an excess of the alcohol used, and, if necessary, in the presence of a water-binding agent and/or while removing the water of reaction by distillation, for example azeotropic distillation, and/or at elevated temperature. The reaction with a reactive derivative of the corresponding alcohol can be carried out in customary manner; when starting from a carboxylic, phosphorous, sulphurous or carbonic acid ester, the reaction is carried out, for example, in the presence of an acidic catalyst, such as one of those mentioned above, in an inert solvent, for example toluene, or in an excess of the alcohol derivative used or in an excess of the corresponding alcohol, if necessary while distilling off the water of reaction, for example azeotropically When starting from a mineral or sulphonic acid ester, the acid to be esterified is advantageously reacted in the form of a salt, for example the sodium or potassium salt, and the operation is carried out, if necessary, in the presence of a basic condensation agent, such as an inorganic base, for example sodium, potassium or calcium hydroxide or carbonate, or a tertiary organic nitrogen base, for example triethylamine or pyridine, and/or in an inert solvent, such as one of the above tertiary nitrogen bases, or a polar solvent, for example dimethylformamide, and/or at elevated temperature. The reaction with an olefin can be carried out, for example, in the presence of an acidic catalyst, for example a Lewis acid, for example boron trifluoride, a sulphonic acid, for example p-toluenesulphonic acid, or, especially, a basic catalyst, for example sodium or potassium hydroxide, advantageously in an inert solvent, such as an ether, for example diethyl ether or tetrahydrofuran.

A free carboxy group $R_6$, $R_7$ and/or $R_8$ can also be converted in customary manner into an amidated carboxy group by reaction with ammonia or an amine having at least one hydrogen atom, while dehydrating the ammonium salt formed as an intermediate, for example by azeotropic distillation with benzene or toluene or by dry heating.

The above-described conversions of carboxy into esterified or amidated carboxy groups can, however, alternatively be carried out as follows: a compound of the formula I in which $R_6$, $R_7$ and/or $R_8$ represent carboxy is first converted in customary manner into a reactive derivative, for example is converted by means of a halide of phosphorus or sulphur, for example by means of phosphorus trichloride or tribromide, phosphorus pentachloride or thionyl chloride, into an acid halide or, by reaction with a corresponding alcohol or amine, into a reactive ester, that is to say an ester having electron-attracting structures, such as an ester with phenol, thiophenol, p-nitrophenol or cyanomethyl alcohol, or into a reactive amide, for example the amide derived from imidazole or 3,5-dimethylpyrazole and the reactive derivative obtained can then be reacted in customary manner, for example as described below for the transesterification, transamidation or conversion into one another of esterified and amidated carboxy groups, with a corresponding alcohol, ammonia or the corresponding amine having at least one hydrogen atom, to form the desired group $R_4$, $R_6$ and/or $R_8$.

An esterified carboxy group $R_6$, $R_7$ and/or $R_8$ and cyano $R_6$ and/or $R_7$ can be hydrolysed to form a free carboxy group, and cyano $R_6$ and/or $R_7$ can also be hydrolysed to form carbamoyl, in customary manner, for example by hydrolysis in the presence of a catalyst, for example a basic or acidic agent, such as a strong base, for example sodium or potassium hydroxide, or a mineral acid, for example hydrochloric acid, sulphuric acid or phosphoric acid. Likewise, esterified carboxy $R_6$, $R_7$ and/or $R_8$ can be converted into an amidated carboxy group, for example by reaction with ammonia or the corresponding amine having at least one hydrogen atom.

An esterified carboxy group $R_6$, $R_7$ and/or $R_8$ can also be transesterified to form a different esterified carboxy group in customary manner, for example by reaction with a metal salt, such as the sodium or potassium salt, of a corresponding alcohol or with the alcohol itself in the presence of a catalyst, for example a strong base, for example sodium or potassium hydroxide, or a strong acid, such as a mineral acid, for example hydrochloric acid, sulphuric acid or phosphoric acid, or an organic sulphonic acid, for example p-toluenesulphonic acid, or a Lewis acid, for example boron trifluoride etherate.

An amidated carboxy group $R_6$, $R_7$ and/or $R_8$ can be converted into a free carboxy group in customary manner, for example by hydrolysis in the presence of a catalyst, for example strong base, such as an alkali metal or alkaline earth metal hydroxide or carbonate, for example sodium or potassium hydroxide or carbonate, or a strong acid, such as a mineral acid, for example hydrochloric acid, sulphuric acid or phosphoric acid.

In a compound obtainable according to the invention it is also possible to introduce substituents into one or both phenyl rings and/or to convert sustituents that are already present into other substituents. For example, lower alkyl can be introduced by reaction with a lower alkyl halide or lower alkene or a lower alkanoic acid halide or anhydride, in each case in the presence of a Lewis acid, such as aluminium trichloride. It is also possible to introduce halogen, for example by treatment with a halogen in the presence of a Lewis acid, such as iron(III) chloride, or by reaction with N-chlorosuccinimide. It is also possible to reduce lower alkenyl or lower alkynyl radicals to form lower alkyl, for example by treatment with hydrogen in the presence of a hydrogenation catalyst, for example palladium-on-carbon. It is also possible to replace halogen, especially iodine, by trifluoromethyl by reaction with trifluoroiodomethane in the presence of copper As mentioned, depending on the starting materials and methods chosen, the novel compounds may be in the form of one of the possible isomers or in the form of a mixture thereof, for example, depending on the number of asymmetrical carbon atoms, they may be in the form of pure optical isomers, such as antipodes, or in the form of isomeric mixtures, such as racemates, diastereoisomeric mixtures or racemic mixtures.

Resulting diastereoisomeric mixtures and racemic mixtures can be separated in known manner on the basis of the physico-chemical differences between the constituents into the pure isomers, diastereoisomers or racemates, for example by chromatography and/or fractional crystallisation.

Resulting racemates can also be resolved into the optical antipodes according to known methods, for example by recrystallisation from an optically active solvent, with the aid of micro-organisms, or by reacting an acidic end product with an optically active base that forms salts with the racemic acid and separating the resulting salts, for example on the basis of their different solubilities, into the diastereoisomers from which the antipodes can be freed by the action of suitable agents. Advantageously, the more active of the two antipodes is isolated.

Resulting free compounds of the formula I, for example those in which $R_6$ and/or $R_7$ represent carboxy and/or $R_8$ represents cartoxy or 5-tetrazolyl, can be converted into salts in a manner known per se, for example by treatment with a base or with a suitable salt of a carboxylic acid, customarily in the presence of a solvent or diluent.

Resulting salts can be converted in a manner known per se into the free compounds, or resulting free compounds in which $R_8$ is capable of forming acid addition salts can be converted in a manner known per se into their acid addition salts, for example by treatment with an acidic reagent, such as mineral acid or one of the mentioned salt-forming acids.

The compounds, including their salts, can also be obtained in the form of their hydrates or can include the solvent used for crystallisation.

As a result of the close relationship between the novel compounds in free form and in the form of their salts, hereinbefore and hereinafter free compounds and their salts should be understood as being optionally also the corresponding salts and free compounds, respectively, where appropriate with regard to meaning and purpose.

The invention also relates to those embodiments of the process according to which a compound obtainable as intermediate at any stage of the process is used as starting material and the remaining steps are carried out or a starting material is used in the form of a salt and/or racemate or antipode or, especially, is formed under the reaction conditions.

The invention also relates to the novel starting materials and intermediates occurring in the processes according to the invention and their precursors The starting materials and reaction conditions are preferably so chosen that the compounds described above as being especially preferred are obtained.

The present invention also relates to pharmaceutical preparations that contain one of the compounds of the formula I according to the invention or a pharmaceutically acceptable salt thereof The pharmaceutical preparations according to the invention are intended for topical and local, and also enteral, such as oral or rectal, and parenteral administration to and for inhalation by warm-blooded animals and they contain the pharmacological active ingredient alone or together with a pharmaceutically acceptable carrier. The dosage of the active ingredient depends on the species of warm-blooded animal, age and individual condition and also on the method of administration.

The novel pharmaceutical preparations contain, for example, from approximately 10% to approximately 95%, preferably from approximately 20% to approximately 90%, active ingredient. Pharmaceutical preparations according to the invention are, for example, in aerosol or spray form, or in dosage unit forms, such as dragées, tablets, capsules or suppositories, and also ampoules.

The pharmaceutical preparations of the present invention are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium biphosphate, also binders, such as starch pastes, for example corn, wheat, rice or potato starch pastes, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée, cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Colourings or pigments can be added to the tablets or dragée, coatings, for example for identification purposes or to indicate different doses of active ingredient.

Further orally administrable pharmaceutical preparations are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran, and, optionally, also stabilisers.

Inhalation preparations for the treatment of the respiratory system by nasal or buccal administration are, for example, aerosols or sprays which are able to disperse the pharmacological active ingredient in the form of a powder or in the form of drops of a solution or suspension. Preparations having powder-dispersing properties generally contain, in addition to the active ingredient, a liquid propellant gas having a boiling point below room temperature, and, if desired, carriers, such as liquid or solid, non-ionic or anionic surface-active agents and/or diluents. Preparations in which the pharmacological active ingredient is in solution contain, in addition to the active ingredient, a suitable propellant, and also, if necessary, an additional solvent and/or a stabiliser. Instead of the propellant gas, it is also possible to use compressed air, which can be produced as required by means of a suitable compression and release device.

Pharmaceutical preparations for topical and local use are, for example, for the treatment of the skin: lotions and creams that contain a liquid or semi-solid oil-in-water or water-in-oil emulsion, and ointments (these preferably containing a preservative); for the treatment of the eyes: eye drops that contain the active compound in aqueous or oily solution, and eye ointments that are preferably manufactured in sterile form; for the treatment of the nose: powders, aerosols and sprays (similar to those described above for the treatment of the respiratory system), and coarse powders that are administered by rapid inhalation through the nostrils, and nose drops that contain the active compound in aqueous or oily solution; or, for the local treatment of the mouth: lozenges that contain the active compound in a composition that is generally formed from sugar and gum arabic or tragacanth and to which flavourings may be added, and pastilles that contain the active ingredient in an inert composition, for example of gelatine and glycerine or sugar and gum arabic.

The invention relates also to the use of the novel compounds of the formula I and their salts as pharmacologically active compounds, for example as anti-allergic agents or especially as anti-inflammatory agents, preferably in the form of pharmaceutical preparations. The daily dose administered to a warm-blooded animal weighing approximately 70 kg is from approximately 200 mg to approximately 1200 mg.

The following Examples illustrate the invention described above, but they are not intended to limit its scope in any way. Temperatures are given in degrees Centigrade.

EXAMPLE 1

In the course of approximately 5 minutes a solution of 1.9 ml (21 mmol) of chloro-oxalic acid methyl ester in 8 ml of methylene chloride is added dropwise to a solution, cooled to 0°, of 7.5 g (21 mmol) of 3-[3-(4-acetyl-3-hydroxy-2-n-propylphenoxy)-propoxy]-6-methylaniline and 3.0 g (21 mmol) of triethylamine in 60 ml of methylene chloride. The reaction mixture is stirred for 90 minutes at room temperature, is poured onto ice-water and the organic phase is separated off. The methylene chloride phase is washed with water, dried over sodium sulphate and concentrated under reduced pressure. Crystallisation of the residue from methylene chloride/ether yields N-{3-[3-(4-acetyl-3-hydroxy-2-n-propylphenoxy)-propoxy]-6-methylphenyl}-oxamic acid methyl ester having a melting point of 125°–127°.

In analogous manner, there are obtained N-3-[3-(4-acetyl-3-hydroxy-2-n-propyl-phenoxy]-4-cyano-6-methylphenyl-oxamic acid, starting from 3-[3-(4-acetyl-3-hydroxy-2-n-propylphenoxy)-propoxy]-aniline, and N- 3-[3-(4-acetyl-3-hydroxy-2-n-propyl-phenoxy]-4-cyano-6-methylphenyl -oxamic acid ethyl ester having a melting point of 142°–144°, starting from 3-[3-(4-acetyl-3-hydroxy-2-n-propyl-phenoxy)-propyloxy]-4-cyano-6-methyl-aniline.

The starting material can be manufactured, for example, as follows:

A spatula tip of potassium iodide and 9.5 g (30 mmol) of 4-(3-bromopropoxy)-2-hydroxy-3-propylacetophenone are added to a suspension of 5.1 g (33 mmol) of 4-methyl-3-nitrophenol and 4.6 g (33 mmol) of calcined potassium carbonate in 100 ml of ethyl methyl ketone and the whole is heated under reflux for 14 hours. The reaction mixture is cooled, poured onto water and extracted three times with ether. The organic phases are washed with water, combined, dried over sodium sulphate and concentrated to dryness under reduced pressure. Crystallisation cf the residue yields 3-[3-(4-acetyl-3-hydroxy-2-n-propylphenoxy)-propoxy]-6-methylnitrobenzene having a melting point of 90°–91°.

In analogous manner, starting from m-nitrophenol, there are obtained 3-[3-(4-acetyl-3-hydroxy-2-n-propyl-phenoxy)-propoxy]-nitrobenzene having a melting point of 71°–72° and 3-[3-(4-acetyl-3-hydroxy-2-n-propylphenoxy)-propyloxy]-4-cyano-nitrobenzene.

1.0 g of Raney nickel is added to a solution of 9.1 g (23.5 mmol) of 3-[3-(4-acetyl-3-hydroxy-2-n-propyl-phenoxy)-propoxy]-6-methylnitrobenzene in 90 ml of tetrahydrofuran and the whole is hydrogenated at room temperature. The catalyst is filtered off and washed with tetrahydrofuran. The filtrate is concentrated to dryness by evaporation under reduced pressure. 3-[3-(4-acetyl-3-hydroxy-2-n-propylphenoxy)-propoxy]-6-methylaniline is obtained having an $R_f$ value=0.12 (silica gel/methylene chloride).

In analogous manner, starting from 3-[3-(4-acetyl-3-hydroxy-2-n-propylphenoxy)-propoxy]-nitrobenzene and from 3-[3-(4-acetyl-3-hydroxy-2-n-propylphenoxy)-propyloxy]-4-cyano-nitrobenzene, there are obtained 3-[3-(4-acetyl-3-hydroxy-2-n-propylphenoxy)-propoxy]-aniline having a melting point of 76°–77° (ether/petroleum ether) and 3-[3-(4-acetyl-3-hydroxy-2-n-propyl-phenoxy)-propyloxy]-4-cyano-aniline.

EXAMPLE 2

20 ml of 1N sodium hydroxide solution are added to a suspension of 8.60 g (19.4 mmol) of N-{3-[3-(4-acetyl-3-hydroxy-2-n-propylphenoxy)-propoxy]-6-methylphenyl}-oxamic acid methyl ester in 60 ml of methanol and 20 ml of water and the whole is heated under reflux for 10 minutes. The reaction mixture is cooled and the product that has formed out is filtered off. The sodium salt of N-{3-[3-(4-acetyl-3-hydroxy-2-n-propylphenoxy)-propoxy]-6-methylphenyl}-oxamic acid having a melting point of 200°–203° is obtained.

In analogous manner, the sodium salts of N-{3-[3-(4-acetyl-3-hydroxy-2-n-propylphenoxy)-propoxy]-phenyl}-oxamic acid having a melting point of above 200° (decomposition) and of N-{3-[3-(4-acetyl-3-hydroxy-2-n-propyl-phenoxy]-4-cyano-6-methyl-phenyl}-oxamic acid having a melting point of 140°–141° (decomposition) can be manufactured.

EXAMPLE 3

In the course of approximately 5 minutes a solution of 3.2 ml of chloro-oxalic acid methyl ester in 10 ml of methylene chloride is added dropwise to a solution, cooled to 0°, of 14.0 g (32 mmol) of 3-[3-(4-acetyl-3-hydroxy-2-n-propylphenoxy)-propoxy]-4-bromo-6-methylaniline and 4.9 ml of triethylamine in 140 ml of methylene chloride and the whole is then stirred at room temperature for a further 90 minutes. The reaction mixture is poured onto ice-water and the organic phase is separated off, washed with water, dried over sodium sulphate and concentrated under reduced pressure. Crystallisation from ethyl acetate/ether/petroleum ether yields N-{3-[3-(4-acetyl-3-hydroxy-2-n-propyl-phenoxy)-propoxy]-4-bromo-6-methylphenyl}-oxamic acid methyl ester having a melting point of 92°–93°.

In analogous manner there are obtained:
N-{3-[3-(4-acetyl-3-hydroxy-2-n-propylphenoxy)-propoxy]-2-methylphenyl}-oxamic acid methyl ester having a melting point of 108°–110° (ethyl acetate/petroleum ether);
N-{3-[3-(4-acetyl-3-hydroxy-2-n-propylphenoxy)-propoxy]-4-iodo-6-methyl-phenyl}-oxamic acid ethyl ester having a melting point of 115°–116°;
N-{3-[5-(4-acetyl-3-hydroxy-2-n-propylphenoxy)-pentyloxy]-phenyl}-oxamic acid methyl ester having a melting point of 108°–109° (methylene chloride/ether);
N-{3-[3-(4-acetyl-3-hydroxy-2-n-propylphenoxy)-propoxy]-4-chloro-6-trifluoromethylphenyl}-oxamic acid methyl ester having a melting point of 109°–110° (ether/petroleum ether);
N-{3-[3-(4-acetyl-3-hydroxy-2-n-propylphenoxy)-propoxy]-2,4,6-trichlorophenyl}-oxamic acid methyl ester in the form of an oil having an $R_f$ value=0.17 (silica gel/methylene chloride), and
N-{3-[3-(4-acetyl-3-hydroxy-2-n-propylphenoxy)-propoxy]-4,6-dimethylphenyl}-oxamic acid methyl ester having a melting point of 111°–112° (ethyl acetate/petroleum ether).

The starting materials can be manufactured, for example, as follows:

A spatula tip of potassium iodide and 14.7 g (46.6 mmol) of 4-(3-bromopropoxy)-2-hydroxy-3-n-propylacetophenone are added to a suspension of 9.8 g (42 mmol) of 2-bromo-4-methyl-5-nitrophenol and 6.4 g (46.6 mmol) of calcined potassium carbonate in 100 ml of ethyl methyl ketone and the whole is heated under reflux for 7 hours. The reaction mixture is cooled, poured onto water and extracted three times with ether. The organic phases are washed with water, combined, dried over sodium sulphate and concentrated under reduced pressure. Crystallisation of the residue yields 3-[3-(4-acetyl-3-hydroxy-2-n-propylphenoxy)-propoxy]-4-bromo-6-methylnitrobenzene having a melting point of 100°–101° (ether).

In analogous manner there are obtained:
3-[3-(4-acetyl-3-hydroxy-2-n-propylphenoxy)-propoxy]-2-methylnitrobenzene having a melting point of 79°–80° (ether);
3-[3-(4-acetyl-3-hydroxy-2-n-propylphenoxy)-propoxy]-4-iodo-6-methyl-nitrobenzene;
3-[5-(4-acetyl-3-hydroxy-2-n-propylphenoxy)-pentyloxy]-nitrobenzene having a melting point of 52°–54°;

3-[3-(4-acetyl-3-hydroxy-2-n-propylphenoxy)-propoxy]-4-chloro-6-trifluoromethylnitrobenzene having a melting point of 112°-113° (ethanol);

3-[3-(4-acetyl-3-hydroxy-2-n-propylphenoxy)-propoxy]-2,4,6-trichloronitrobenzene having a melting point of 91°-92° (ether/petroleum ether), and 3-[3-(4-acetyl-3-hydroxy-2-n-propylphenoxy)-propoxy]-4,6-dimethylnitrobenzene having a melting point of 89°-91° (ether/petroleum ether).

3.0 g of Raney nickel are added to a solution of 15.9 g (34.1 mmol) of 3-[3-(4-acetyl-3-hydroxy-2-n-propylphenoxy)-propoxy]-4-bromo-6-methylnitrobenzene in 160 ml of tetrahydrofuran and the whole is hydrogenated at room temperature. The catalyst is filtered off and washed with tetrahydrofuran. The filtrate is concentrated to dryness by evaporation under reduced pressure. 3-[3-(4-acetyl-3-hydroxy-2-n-propylphenoxy)-propoxy]-4-bromo-6-methylaniline having a melting point of 108°-109° is obtained (ether/petroleum ether).

In analogous manner there are obtained: 3-[3-(4-acetyl-3-hydroxy-2-n-propylphenoxy)-propoxy]-2-methylaniline having a melting point of 99°-100° (ether/petroleum ether);

3-[3-(4-acetyl-3-hydroxy-2-n-propylphenoxy)-propoxy]-4-iodo-6-methyl-aniline;

3-[5-(4-acetyl-3-hydroxy-2-n-propylphenoxy)-pentyloxy]-aniline in the form of an oil having an $R_f$ value=0.44 (silica gel; methylene chloride/ethyl acetate=10:1);

3-[3-(4-acetyl-3-hydroxy-2-n-propylphenoxy)-propoxy]-4-chloro-6-trifluoromethylaniline having a melting point of 107°-108° (methanol);

3-[3-(4-acetyl-3-hydroxy-2-n-propylphenoxy)-propoxy]-2,4,5-trichloroaniline having a melting point of 57°-58°, and 3-[3-(4-acetyl-3-hydroxy-2-n-propylphenoxy)-propoxy]-4,6-dimethylaniline having a melting point of 72°-73° (ether/petroleum ether).

EXAMPLE 4

A suspension of 15.1 g (29 mmol) of N-{3-[3-(4-acetyl-3-hydroxy-2-n-propylphenoxy)-propoxy]-4-bromo-6-methylphenyl}-oxamic acid methyl ester in 120 ml of methanol and 30.4 ml of N sodium hydroxide solution is heated under reflux for 90 minutes. The reaction mixture is concentrated under reduced pressure, dissolved in acetone and dilute sodium hydroxide solution and acidified with dilute hydrochloric acid. The product that has formed is filtered off, washed with acetone/water and recrystallised from isopropanol. N-{3-[3-(4-acetyl-3-hydroxy-2-n-propylphenoxy)-propoxy]-4-bromo-6-methylphenyl}-oxamic acid having a melting point of 191°-192° is obtained. 10.9 g (21.5 mmol) of this product are dissolved in 450 ml of isopropanol under reflux, and a solution of 3.20 g (21.5 mmol) of triethanolamine in 30 ml of isopropanol is then added thereto. The solution is cooled and concentrated to approximately one third under reduced pressure. After the addition of ether, crystallisation begins. The product that has formed is filtered off and washed with ether. The triethanolammonium salt of N-{3-[3-(4-acetyl-3-hydroxy-2-n-propylphenoxy)-propoxy]-4-bromo-6-methylphenyl}-oxamic acid having a melting point of 85°-86° is obtained.

In analogous manner, starting from N-{3-[3-(4-acetyl-3-hydroxy-2-n-propylphenoxy)-propoxy]-2-methylphenyl}-oxamic acid methyl ester there is obtained N-{3-[3-(4-acetyl-3-hydroxy-2-n-propylphenoxy)-propoxy]-2-methylphenyl}-oxamic acid having a melting point of 146°-148° (toluene) and the triethanolammonium salt thereof having a melting point of 114°-115°, Starting from N- 3-(4-acetyl-3-hydroxy-2-n-propylpnenoxy)-propoxy]-4-iodo-6-methyl-phenyl -oxamic acid ethyl ester there is obtained N- 3-[3-(4-acetyl-3-hydroxy-2-n-propylphenoxy)-propoxy]-4-iodo-6-methylphenyl-oxamic acid and the sodium salt thereof (melting point 119°-121°);

starting from N-[3-(5-[4-acetyl-3-hydroxy-2-n-propylphenoxy]-pentyloxy)-phenyl]-oxamic acid methyl ester there is obtained N-{3-[5-(4-acetyl-3-hydroxy-2-n-propylphenoxy)-pentyloxy]-phenyl}-oxamic acid having a melting point of 117°-118° (toluene) and the triethanolammonium salt thereof, starting from N-{3-[3-(4-acetyl-3-hydroxy-2-n-propylphenoxy)-propoxy]-4-chloro-6-trifluoromethylphenyl}-oxamic acid methyl ester there is obtained N-{3-[3-(4-acetyl-3-hydroxy-2-n-propylphenoxy)-propoxy]-4-chloro-6-trifluoromethylphenyl}-oxamic acid having a melting point of 173°-174° and the triethanolammonium salt thereof having a melting point of 94°-95°, starting from N-{3-[3-(4-acetyl-3-hydroxy-2-n-propylphenoxy)-propoxy]-2,4,6-trichlorophenyl}-oxamic acid methyl ester there is obtained N-{3-[3-(4-acetyl-3-hydroxy-2-n-propylphenoxy)-propoxy]-2,4,6-trichlorophenyl}-oxamic acid having a melting point of 151°-152° (ether/petroleum ether) and the triethanolammonium salt thereof, and, starting from N-{3-[3-(4-acetyl-3-hydroxy-2-n-propylphenoxy)-propoxy]-4,6-dimethylphenyl}-oxamic acid methyl ester there is obtained N-{3-[3-(4-acetyl-3-hydroxy-2-n-propylphenoxy)-propoxy]-4,6-dimethylphenyl}-oxamic acid having a melting point of 197°-198° (ethyl acetate/petroleum ether) and the triethanolammonium salt thereof.

EXAMPLE 5

2.25 g (50 mmol) of 55% sodium hydride suspension in mineral oil are added to a solution of 8.45 g (50 mmol) of 2-methoxy-4-nitrophenol in 100 ml of N,N-dimethylformamide. The whole is then heated to 40° and a solution of 15.7 g (50 mmol) of 4-(3-bromopropoxy)-2-hydroxy-3-n-propylacetophenone in 30 ml of N,N-dimethylformamide is added dropwise thereto in the course of approximately 10 minutes and the mixture is then kept at this temperature for a further 6 hours. The reaction mixture is concentrated under reduced pressure, diluted with water and extracted three times with methylene chloride. The organic phases are washed with ater, combined, dried over sodium sulphate and concentrated to dryness by evaporation under reduced pressure. The residue is chromatographed over silica gel using methylene chloride as eluant. Crystallisation of the fractions that are pure according to thin-layer chromatography yields 4-[3-(4-acetyl-3-hydroxy-2-n-propylphenoxy)-propoxy]-3-methoxynitrobenzene having a melting point of 109°-111°.

In analogous manner there are obtained

4-[3-(4-acetyl-3-hydroxy-2-n-propylphenoxy)-propoxy]-2-methylnitrobenzene having a melting point of 76°-77°;

2-[3-(4-acetyl-3-hydroxy-2-n-propylphenoxy)-propoxy]-nitrobenzene having a meltirg point of 103°-104° (ether), and 4-[3-(4-acetyl-3-hydroxy-2-n-propylphenoxy)-propoxy]-nitrobenzene having a melting point of 98°–99° (ethyl acetate/ether/petroleum ether).

The reduction of the nitro group to the amino group using hydrogen and Raney nickel in tetrahydrofuran is carried out using a method analogous to that described in Example 1. There are thus obtained from the nitro compounds described above:

4-[3-(4-acetyl-3-hydroxy-2-n-propylphenoxy)-propoxy]-3-methoxyaniline having a melting point of 68°–69° (ether/petroleum ether);

4-[3-(4-acetyl-3-hydroxy-2-n-propylphenoxy)-propoxy]-2-methylaniline having a melting point of 81°–82° (ether/petroleum ether);

2-[3-(4-acetyl-3-hydroxy-2-n-propylphenoxy)-propoxy]-aniline in the form of an oil, and 4-[3-(4-acetyl-3-hydroxy-2-n-propylphenoxy)-propoxy]-aniline having a melting point of 76°–77° (ethyl acetate/petroleum ether).

The reaction of these aniline compounds with chlorooxalic acid methyl ester and triethylamine in methylene chloride to form the oxamic acid esters is effected as described in Example 1 The following compounds are thus obtained from the aniline compounds described above:

N-{4-[3-(4-acetyl-3-hydroxy-2-n-propylphenoxy)-propoxy]-3-methoxyphenyl}-oxamic acid methyl ester having a melting point of 135°–136° (methylene chloride/ether);

N-{4-[3-(4-acetyl-3-hydroxy-2-n-propylphenoxy)-propoxy]-2-methylphenyl}-oxamic acid methyl ester having a melting point of 116°–117° (ether/petroleum ether);

N-{2-[3-(4-acetyl-3-hydroxy-2-n-propylphenoxy)-propoxy]-phenyl}-oxamic acid methyl ester having a melting point of 110°–111° (ethyl acetate/ether), and N-{4-[3-(4-acetyl-3-hydroxy-2-n-propylphenoxy)-propoxy]-phenyl}-oxamic acid methyl ester having a melting point of 135°–136° (ethyl acetate/ether/petroleum ether).

EXAMPLE 6

18 ml of an N sodium hydroxide solution are added to a solution of 7.95 g (17.3 mmol) of N-{4-[3-(4-acetyl-3-hydroxy-2-n-propylphenoxy)-propoxy]-3-methoxyphenyl}-oxamic acid methyl ester in 100 ml of methanol and the whole is heated for one hour under reflux. The hot solution is then poured into 200 ml of 0.1N hydrochloric acid. The product that has formed is filtered off, washed with water and dried in a drying cabinet over phosphorus pentoxide. The resulting N-{4-[3-(4-acetyl-3-hydroxy-2-n-propylphenoxy)-propoxy]-3-methoxyphenyl}-oxamic acid having a melting point of 156°–157° is again dissolved in 100 ml of methanol while hot, and one equivalent of triethanolamine in 10 ml of methanol is added thereto. After the addition of 400 ml of ether, crystallisation begins. The triethanolammonium salt of N-{4-[3-(4-acetyl-3-hydroxy-2-n-propylphenoxy)-propoxy]-3-methoxyphenyl}-oxamic acid having a melting point of 125°–127° is obtained.

In analogous manner, starting from N-{4-[3-(4-acetyl-3-hydroxy-2-n-propylphenoxy)-propoxy]-2-methylphenyl}-oxamic acid methyl ester there is obtained N-{4-[3-(4-acetyl-3-hydroxy-2-n-propylphenoxy)-propoxy]-2-methylphenyl}-oxamic acid having a melting point of 164°–165° (ethyl acetate/petroleum ether) and the triethanolammonium salt thereof having a melting point of 103°–104°;

starting from N-{2-[3-(4-acetyl-3-hydroxy-2-n-propylphenoxy)-propoxy]-phenyl}-oxamic acid methyl ester there is obtained N-{2-[3-(4-acetyl-3-hydroxy-2-n-propylphenoxy)-propoxy]-phenyl}-oxamic acid having a melting point of 164°–165° (ethyl acetate/petroleum ether) and the triethanolammonium salt thereof, and, starting from N-[4-(3-[4-acetyl-3-hydroxy-2-n-propylphenoxy]-propoxy)-phenyl]-oxamic acid methyl ester there is obtained N-{4-[3-(4-acetyl-3-hydroxy-2-n-propylphenoxy)-propoxy]-phenyl}-oxamic acid having a melting point of 145°–146° (acetone/ether/petroleum ether) and the triethanolammonium salt thereof having a melting point of 111°–112°.

EXAMPLE 7

A solution of 5.6 g (8.58 mmol) of N-{3-[3-(4-acetyl-3-hydroxy-2-n-propylphenoxy)-propoxy]-4-bromo-6-methylphenyl}-1-(4-methoxybenzyl)-tetrazole-5-carboxamide in 150 ml of trifluoroacetic acid and 15 ml of anisole is heated under reflux for 30 minutes. The reaction mixture is concentrated under reduced pressure, approximately 200 ml of ether and 300 ml of petroleum ether are added and the crystals are filtered off. The resulting N-{3-[3-(4-acetyl-3-hydroxy-2-n-propylphenoxy)-propoxy]-4-bromo-6-methylphenyl}-1H-tetrazole-5-carboxamide having a melting point of 236°–238° is dissolved in 150 ml of tetrahydrofuran while hot, and one equivalent of triethanolamine in 20 ml of tetrahydrofuran is added thereto. After the addition of ether, crystallisation begins. The triethanolammonium salt of N-{3-[3-(4-acetyl-3-hydroxy-2-n-propylphenoxy)-propoxy]-4-bromo-6-methylphenyl}-1H-tetrazole-5-carboxamide having a melting point of 63°–65° is obtained.

In analogous manner, starting from N-{3-[3-(4-acetyl-3-hydroxy-2-n-propylphenoxy)-propoxy]-phenyl}-1-(4-methoxybenzyl)-tetrazole-5-carboxamide or N- 3-[3-(4-acetyl-3-hydroxy-2-n-propylphenoxy)-pentyloxy]-4-chloro-6-methyl-phenyl -1-(4-methoxybenzyl)-tetrazole-5-caboxamide, resp. there are obtained N- 3-[3-(4-acetyl-3-hydroxy-2-n-propylphenoxy)-propoxy]-phenyl -1H-tetrazole-5-carboxamide having a melting point of 176°–178° (ethyl acetate/petroleum ether) and the triethanolammonium salt thereof having a melting point of 118°–119° (acetone/ether) as well as N- 3-[3-(4-acetyl-3-hydroxy-2-n-propylphenoxy)pentyloxy]-4-chloro-6-methyl-phenyl-1H-tetrazole-5-carboxamide having a melting point of 176°–178° (ethyl acetate/petroleum ether) and the sodium salt therof.

The starting materials are obtained, for example, as follows:

At 0°–5°, 1.84 ml (21.5 mmol) of oxalyl chloride are added to a suspension of 5.8 g (21.5 mmol) of potassium {1-(4-methoxybenzyl)-tetrazole}-5-carboxylate in 110 ml of benzene and 1.0 ml of pyridine and the whole is stirred for 30 minutes at room temperature. The reaction mixture is concentrated under reduced pressure, the residue is taken up in benzene and the whole is again concentrated by evaporation under reduced pressure. The residue is dissolved in 80 ml of methylene chloride and, at 0°–5°, the resulting solution is added dropwise in the course of approximately 10 minutes to a solution of 7.5 g (17.2 mmol) of 3-[3-(4-acetyl-3-hydroxy-2-n-propylphenoxy)-propoxy]-4-bromo-6-methylaniline (Example 3) and 1.72 ml (21.5 mmol) of pyridine in 40 ml of methylene chloride. The mixture is then stirred at room temperature for 3 hours. The reaction mixture is diluted with methylene chloride and washed three times with water. The organic phases are combined, dried over sodium sulphate and concentrated by evaporation under reduced pressure Crystallisation of the residue from methylene chloride/ether yields N-{3-[3-(4-acetyl-3-hydroxy-2-n-propylphenoxy)-propoxy]-4-bromo-6-methylphenyl}-1-(4-methoxybenzyl)-tetrazole-5-carboxamide having a melting point of 146°-147°.

Analogously, starting from 3-[3-(4-acetyl-3-hydroxy-2-n-propylphenoxy)-propoxy]-aniline (Example 3) and the potassium salt of 1-(4-methoxybenzyl)-tetrazolyl-5-carboxylic acid there is obtained N-{3-[3- (4-acetyl-3-hydroxy-2-n-propylphenoxy)-propoxy]-phenyl}-1-(4-methoxybenzyl)-tetrazole-5-carboxamide having a melting point of 141°-142° (ether/petroleum ether).

In an analogous manner as described in Example 3, 4-(5-pentyloxy)-2-hydroxy-3-n-acetophenone is reacted with 2-chloro-4-methyl-5-nitrophenol which is reduced yielding 3-[5-(4-acetyl-3-hydroxy-2-n-propylphenoxy]-4-chloro-6-methyl-aniline which is then further reacted with potassium{1-(4-methoxybenzyl)-tetrazole}-5-carboxylate.

EXAMPLE 8

In the course of approximately 5 minutes a solution of 12.3 ml of chloro-oxalic acid ethyl ester in 30 ml of methylene chloride is added dropwise to a solution, cooled to 0° C., of 43.6 g (100 mmol) of 3-[3-(4-acetyl-3-hydroxy-2-n-propylphenoxy)-propoxy]-4-bromo-6-methylaniline and 15.3 ml of triethylamine in 400 ml of methylene chloride and the whole is then stirred for a further 90 minutes at room temperature. The reaction mixture is poured onto ice-water and the organic phase is separated off, washed with water, dried over sodium sulphate and concentrated under reduced pressure. Crystallisation from ethyl acetate/ether/petroleum ether yields N-{3-[3-(4-acetyl-3-hydroxy-2-n-propylphenoxy)-propoxy]-4-bromo-6-methylphenyl}-oxamic acid ethyl ester having a melting point of 100°-102°.

EXAMPLE 9

448 mg (7.5 mmol) of potassium hydroxide are added to a suspension of 4.0 g (7.46 mmol) of N-{3-[3-(4-acetyl-3-hydroxy-2-n-propylphenoxy)-propoxy]-4-bromo-6-methylphenyl}-oxamic acid ethyl ester in 400 ml of ethanol and the whole is heated under reflux for 4 hours. The reaction mixture is cooled and the product that has formed is filtered off. The potassium salt of N-{3-[3-(4-acetyl-3-hydroxy-2-n-propylphenoxy)-propoxy]-4-bromo-6-methylphenyl-3-oxamic acid having a melting point of 117°-119° is obtained.

In analogous manner it is also possible to manufacture the sodium salt of N-{3-[3-(4-acetyl-3-hydroxy-2-n-propylphenoxy)-propoxy]-4-bromo-6-methylphenyl}-oxamic acid having a melting point of 215° (decomposition).

EXAMPLE 10

4.06 g (8 mmol) of N-{3-[3-(4-acetyl-3-hydroxy-2-n-propylphenoxy)-propoxy]-4-bromo-6-methylphenyl}-oxamic acid are dissolved in 40 ml of acetone, and a solution of 840 mg (8 mmol) of diethanolamine in 5 ml of acetone is added thereto. After the addition of ether, crystallisation begins. The product that has formed is filtered off and washed with ether. The diethanolammonium salt of N-{3-[3-(4-acetyl-3-hydroxy-2-n-propylphenoxy)-propoxy]-4-bromo-6-methylphenyl}-oxamic acid having a melting point of 101°-103° is obtained.

In analogous manner it is also possible to manufacture the tris-(hydroxymethyl)-methylammonium salt of N-{3-[3-(4-acetyl-3-hydroxy-2-n-propylphenoxy)-propoxy]-4-bromo-6-ethylphenyl}-oxamic acid having a melting point of 88°-90°.

EXAMPLE 11

A solution of 7.05 g (12.06 mmol) of N-{3-[3-(4-acetyl-3-hydroxy-2-n-propylphenoxy)-propoxy]-2-cyanophenyl}-1-(4-methoxybenzyl)-tetrazole-5-carboxamide in 150 ml of trifluoroacetic acid and 15 ml of anisole is heated under reflux for 30 minutes. The reaction mixture is concentrated under reduced pressure, approximately 200 ml of ether and 300 ml of petroleum ether are added and the crystals are filtered off. The resulting N-{3-[3-(4-acetyl-3-hydroxy-2-n-propylphenoxy)-propoxy]- 2-cyanophenyl}-1H-tetrazole-5-carboxamide having a melting point of 206°-208° is dissolved in 50 ml of acetone while hot, and the calculated amount of triethanolamine in 30 ml of acetone is added thereto. After the addition of ether, crystallisation begins. The triethanolammonium salt of N-{3-[3-(4-acetyl-3-hydroxy-2-n-propylphenoxy)-propoxy]-2-cyanophenyl}-1H-tetrazole-5-carboxamide having a melting point of 81° (decomposition) is obtained.

The starting material can be manufactured, for example, as follows:

A spatula tip of potassium iodide and 31.5 g (100 mmol) of 4-(3-bromopropoxy)-2-hydroxy-3-propylacetophenone are added to a suspension of 13.1 g (80 mmol) of 2-cyano-3-nitrophenol and 13.8 g (100 mmol) of calcined potassium carbonate in 100 ml of ethyl methyl ketone and the whole is heated for 20 hours under reflux. The reaction mixture is cooled, poured onto water and extracted three times with methylene chloride. The organic phases are washed with water, combined, dried over sodium sulphate and concentrated to dryness under reduced pressure. Crystallisation of the residue from ether/hexane yields 2-[3-(4-acetyl-3-hydroxy-2-propylphenoxy)-propoxy]-6-nitrobenzonitrile having a melting point of 88°-88°.

2.5 g of 10% palladium-on-carbon are added to a solution of 10 g (25.1 mmol) of 2-[3-(4-acetyl-3-hydroxy-2-propylphenoxy)-propoxy]-6-nitrobenzonitrile and 10 g of cyclohexene in 500 ml of ethanol and the whole is heated under reflux for 30 minutes. After cooling to room temperature the mixture is filtered and freed of solvent. Ether is added to the residue and the crystals that have separated out are filtered off. 2-amino-6-[3-(4-acetyl-3-hydroxy-2-n-propylphenoxy)-propoxy]-benzonitrile having a melting point of 120°-122° C. is obtained.

At 0°-5°, 1.84 ml (21.5 mmol) of oxalyl chloride are added to a suspension of 5.8 g (21.5 mmol) of potassium {1-(4-methoxybenzyl)-tetrazole}-5-carboxylate in 110 ml of benzene and 1.0 ml of pyridine and the whole is stirred at room temperature for 30 minutes. The reaction mixture is concentrated under reduced pressure, the residue is taken up in benzene and again concentrated by evaporation under reduced pressure. The residue is dissolved in 80 ml of methylene chloride and, at 0°-5°, is added dropwise in the course of approximately 10 minutes to a solution of 6.3 g (17.2 mmol) of 2-amino-6-[3-(4-acetyl-3-hydroxy-2-n-propylphenoxy)-propoxy]-benzonitrile and 1.72 ml (21.5 mmol) of pyridine in 40 ml of methylene chloride. The mixture is then stirred for 3 hours at room temperature. The reaction mixture is diluted with methylene chloride and washed three times with water. The organic phases are combined, dried over sodium sulphate and concentrated by evaporation under reduced pressure. Crystallisation of the residue from ethyl acetate/hexane yields N-{3-[3-(4-acetyl-3-hydroxy-2-n-propylphenoxy)-propoxy]-2-cyanophenyl}-1-(4-methoxybenzyl)-tetrazole-5-carboxamide having a melting point of 137°–139°.

EXAMPLE 12

In the course of approximately 5 minutes a solution of 1.9 ml (21 mmol) of chloro-oxalic acid methyl ester in 8 ml of methylene chloride is added dropwise to a solution, cooled to 0°, of 7.0 g (17.8 mmol) of 3-[3-(4-acetyl-3-hydroxy-2-n-propylphenoxy)-propoxy]-4-methyl-6-chloroaniline and 22.2 g (21.4 mmol) of triethylamine in 100 ml of methylene chloride. The reaction mixture is stirred for a further 90 minutes at room temperature, poured onto ice-water and the organic phase is separated off. The methylene chloride phase is washed with water, dried over sodium sulphate and concentrated under reduced pressure. Crystallisation of the residue from methylene chloride/ether yields N-{3-[3-(4-acetyl-3-hydroxy-2-n-propylphenoxy)-propoxy]-4-methyl-6-chlorophenyl}-oxamic acid methyl ester having a melting point of 101°–102°.

In analogous manner, starting from 3-[3-(4-acetyl-3-hydroxy-2-n-propylphenoxy)-propoxy]-4-chloro-6-methylaniline, there is obtained N-{3-[3-(4-acetyl-3-hydroxy-2-n-propylphenoxy)-propoxy]-4-chloro-6-methyloxamic acid methyl ester having a melting point of 92°–93° C., and, starting from 3-[3-(4-acetyl-3-hydroxy-2-n-propylphenoxy)-propoxy]-4-methyl-6-bromoaniline, there is obtained N-{3-[3-(4-acetyl-3-hydroxy-2-n-propylphenoxy)-propoxy]-4-methyl-6-bromo-phenyl}-oxamic acid methyl ester having a melting point of 100°–101°.

The starting materials are obtained, for example, as follows:

A spatula tip of potassium iodide and 30 g (95 mmol) of 4-(3-bromopropoxy)-2-hydroxy-3-propylacetophenone are added to a suspension of 9.7 g (51 mmol) of 2-methyl-4-chloro-5-nitrophenol and 10 g (72 mmol) of calcined potassium carbonate in 50 ml of ethyl methyl ketone and the whole is heated under reflux for 4 hours. The reaction mixture is cooled, poured onto water and extracted three times with methylene chloride. The organic phases are washed with water, combined, dried over sodium sulphate and concentrated to dryness under reduced pressure. Crystallisation of the residue from methylene chloride/hexane yields 3-[3-(4-acetyl-3-hydroxy-2-n-propylphenoxy)-propoxy]-4-methyl-6-chloronitrobenzene having a melting point of 113°–115° C.

In analogous manner, starting from 2-chloro-4-methyl-5-nitrophenol, there is obtained 3-[3-(4-acetyl-3-hydroxy-2-n-propyl)-propoxy]-4-chloro-6-methylnitrobenzene having a melting point of 96°–98° C., and, starting from 2-methyl-4-bromo-5-nitrophenol, there is obtained 3-[3-(4-acetyl-3-hydroxy-2-n-propyl)-propoxy]-4-methyl-6-bromonitrobenzene having a melting point of 111°–113°.

4.0 g of Raney nickel are added to a solution of 19 g (45 mmol) of 3-[3-(4-acetyl-3-hydroxy-2-n-propylphenoxy)-propoxy]-4-methyl-6-chloronitrobenzene in 200 ml of tetrahydrofuran and the whole is hydrogenated at room temperature. The catalyst is filtered off and washed with tetrahydrofuran. The filtrate is concentrated to dryness by evaporation under reduced pressure and the residue is recrystallised from ether/hexane. 3-[3-(4-acetyl-3-hydroxy-2-n-propylphenoxy)-propoxy]-4-methyl-6-chloroaniline having a melting point of 81° C. is obtained.

In analogous manner, starting from 3-[3-(4-acetyl-3-hydroxy-2-n-propylphenoxy)-propoxy]-4-chloro-6-methylnitrobenzene, there is obtained 3-[3-(4-acetyl-3-hydroxy-2-n-propylphenoxy)-propoxy]-4-chloro-6-methylaniline having a melting point of 119° C., and, starting from 3-[3-(4-acetyl-3-hydroxy-2-n-propylphenoxy)-propoxy]-4-methyl-6-bromonitrobenzene, there is obtained 3-[3-(4-acetyl-3-hydroxy-2-n-propylphenoxy)-propoxy]-4-methyl-6-bromoaniline having a melting point of 97°–99°.

EXAMPLE 13

A suspension of 6.1 g (12.8 mmol) of N-{3-[3-(4-acetyl-3-hydroxy-2-n-propylphenoxy)-propoxy]-4-methyl-6-chlorophenyl}-oxamic acid methyl ester in 200 ml of methanol and 14.1 ml of N sodium hydroxide solution is heated under reflux for 90 minutes. The reaction mixture is concentrated under reduced pressure, dissolved in hot water and, after cooling, acidified with dilute hydrochloric acid. The product that has formed is filtered off, washed with water and recrystallised from acetone. N-{3-[3-(4-acetyl-3-hydroxy-2-n-propylphenoxy)-propoxy]-4-methyl-6-chlorophenyl}-oxamic acid having a melting point of 183°–184° (decomposition) is obtained. The acid is dissolved in 350 ml of acetone, and one equivalent of triethanolamine is added thereto. The solution is concentrated under reduced pressure to approximately one third and ether is added. The product that has formed is filtered off and washed with ether. The triethanolammonium salt of N-{3-[3-(4-acetyl-3-hydroxy-2-n-propylphenoxy)-propoxy]-4-methyl-6-chlorophenyl}-oxamic acid having a melting point of 70° (decomposition) is obtained.

In analogous manner, starting from N-{3-[3-(4-acetyl-3-hydroxy-2-n-propylphenoxy)-propoxy]-4-chloro-6-methylphenyl}-oxamic acid methyl ester, there is obtained N-{3-[3-(4-acetyl-3-hydroxy-2-n-propylphenoxy)-propoxy]-4-chloro-6-methylphenyl}-oxamic acid having a melting point of 188°–189° C. and the triethanolammonium salt thereof having a melting point of 86°–88°.

EXAMPLE 14

A solution of 7.2 g (11.9 mmol) of N-{3-[3-(4-acetyl-3-hydroxy-2-n-propylphenoxy)-propoxy]-4-methyl-6-chlorophenyl}-1-(4-methoxybenzyl)-tetrazole-5-carboxamide in 150 ml of trifluoroacetic acid and 15 ml of anisole is heated under reflux for 30 minutes. The reaction mixture is concentrated under reduced pressure, approximately 200 ml of ether and 300 ml of petroleum ether are added and the crystals are filtered off. The resulting N-{3-[3-(4-acetyl-3-hydroxy-2-n-propylphenoxy)-propoxy]-4-methyl-6-chlorophenyl}-1H-tetrazole-5-carboxamide having a melting point of 213°–215° is dissolved in 70 ml of acetone while hot, and one equivalent of triethanolamine is added thereto. After the addition of ether, crystallisation begins. The triethanolammonium salt having a melting point of 107°–109° is obtained.

In analogous manner, there are obtained:
starting from N- 3-[3-(4-acetyl-3-hydroxy-2-n-propylphenoxy)-propoxy]-4-chloro-6-methylphenyl -1-(4-methoxybenzyl)-tetrazole-5-carboxamide, N-{3-[3-(4-acetyl-3-hydroxy-2-n-propylphenoxy)-propoxy]-4- chloro-6-methylphenyl}-1H-tetrazole-5-carboxamide having a melting point of 234°–235° (decomposition) and the triethanolammonium salt thereof having a melting point of 108°–110°;

starting from N-{3-[3-(4-acetyl-3-hydroxy-2-n-propylphenoxy)-propoxy]-3-methyl-6-bromophenyl}-1-(4-methoxybenzyl)-tetrazole-5-carboxamide, there is obtained N-{3-(4-acetyl-3-hydroxy-2-n-propylphenoxy)-propoxy]-4-methyl-6-bromo-phenyl}-1H-tetrazole-5-carboxamide having a melting point of 212°–214° and the triethanolammonium salt thereof having a melting point of 129°–130° starting from N-{3-[3-(4-acetyl-3-hydroxy-2-n-propylphenoxy)-propoxy]-4-iodo-6-methylphenyl}-1-(4-methoxybenzyl)-tetrazole-5-carboxamide, N-{3-[3-(4-acetyl-3-hydroxy-2-n-propylphenoxy)-propoxy]-4-iodo-6-methylphenyl}-tetrazole-5-carboxamide and the sodium salt thereof having a melting point of 250° (decomposition); and starting from N-{3-[3-(4-acetyl-3-hydroxy-2-n-propylphenoxy)-propoxy]-4-cyano-6-methylphenyl}-1-(4-methoxybenzyl)-tetrazole-5-carboxamide, N-{3-[3-(4-acetyl-3-hydroxy-2-n-propylphenoxy)-propoxy]-4-cyano-6-methylphenyl}-tetrazole-5-carboxamide and the sodium salt thereof having a melting point of 150° (decomposition).

The starting materials are obtained, for example, as follows:

At 0°–5°, 2.03 ml (23.2 mmol) of oxalyl chloride are added to a suspension of 6.3 g (23.2 mmol) of potassium {1-(4-methoxybenzyl)-tetrazole}-5-carboxylate in 70 ml of benzene and 1.0 ml of pyridine and the whole is stirred for 30 minutes at room temperature. The reaction mixture is concentrated under reduced pressure, the residue is taken up in benzene and again concentrated by evaporation under reduced pressure. The residue is dissolved in 80 ml of methylene chloride and, at 0°–5°, added dropwise in the course of approximately 10 minutes to a solution of 7.5 g (17.2 mmol) of 3-[3-(4-acetyl-3-hydroxy-2-n-propylphenoxy)-propoxy]-4-methyl-6-chloroaniline (Example 12) and 1.87 ml (23.2 mmol) of pyridine in 40 ml of methylene chloride. The mixture is then stirred for 3 hours at room temperature. The reaction mixture is diluted with methylene chloride and washed three times with water. The organic phases are combined, dried over sodium sulphate and concentrated by evaporation under reduced pressure Crystallisation of the residue from methylene chloride/ether yields N-{3-[3-(4-acetyl-3-hydroxy-2-n-propylphenoxy)-propoxy]-4-methyl-6-chlorophenyl}-1-(4-methoxybenzyl)-tetrazole-5-carboxamide having a melting point of 132°.

In analogous manner, there are obtained:

starting from 3-[3-(4-acetyl-3-hydroxy-2-n-propylphenoxy)-propoxy]-4-chloro-6-methylaniline (Example 12), N-{3-[3-(4-acetyl-3-hydroxy-2-n-propylphenoxy)-propoxy]-4-chloro-6-methylphenyl}-1-(4-methoxybenzyl)-tetrazole-5-carboxamide having a melting point of 137°–139°;

starting from 3-[3-(4-acetyl-3-hydroxy-2-n-propylphenoxy)-propoxy]-4-methyl-6-bromoaniline (Example 12), there is obtained N-{3-[3-(4-acetyl-3-hydroxy-2-n-propylphenoxy)-propoxy]-4-methyl-6-bromophenyl}-1-(4-methoxybenzyl)-tetrazole-5-carboxamide having a melting point of 122°–123°; starting from 3-[3-(4-acetyl-3-hydroxy-2-n-propylphenoxy)-propyloxy]-4-iodo-6-methylaniline (Example 3) N-{3-[3-(4-acetyl-3-hydroxy-2-n-propylphenoxy)-4-iodo-6-methyl-phenyl}-1-(4-methoxybenzyl)-tetrazole-5-carboxamide; and starting from 3-[3-(4-acetyl-3-hydroxy-2-n-propylphenoxy)-propyloxy]-4-cyano-6-methyl-aniline (Example 1) N-{3-[3-(4-acetyl-3-hydroxy-2-n-propylphenoxy)-4-cyano-6-methyl-phenyl}-1-(4-methoxybenzyl)-tetrazole-5-carboxamide.

EXAMPLE 15

In a manner analogous to that described in Examples 8 and 9, starting from 3-[3-(4-acetyl-3-hydroxy-2-n-propylphenoxy)-propoxy]-2-cyanoaniline, by reaction with chloro-oxalic acid ethyl ester there is obtained N-{3-[3-(4-acetyl-3-hydroxy-2-n-propylphenoxy)-propoxy]-2-cyanophenyl}-oxamic acid ethyl ester having a melting point of 158°–159°, and, by hydrolysis of that compound, N-{3-[3-(4-acetyl-3-hydroxy-2-n-propylphenoxy)-propoxy]-2-cyanophenyl}-oxamic acid is obtained in the form of the triethanolammonium salt having a melting point of 79°–81°.

EXAMPLE 16

In the course of 5 minutes 3.0 g of boron tribromide are added dropwise to a solution, cooled to −78° C., of 2.2 g of N-{3-[3-(4-acetyl-3-methoxy-2-n-propylphenoxy)-propoxy]-phenyl}-oxamic acid ethyl ester in 20 ml of methylene chloride. The whole is then stirred for 6 hours at room temperature. While cooling, 5 ml of water are added and the organic phase is separated off and concentrated by evaporation under reduced pressure. After recrystallisation from methylene chloride/ether there is obtained N-{3-[3-(4-acetyl-3-hydroxy-2-n-propylphenoxy)-propoxy]-phenyl}-oxamic acid ethyl ester, which can be characterised by hydrolysis to form the free acid having a melting point of 159°–160°.

The starting material can be manufactured, for example, as follows:

5530 mg of sodium hydride are added to a solution of 7.46 g of 3-[3-(4-acetyl-3-hydroxy-2-n-propylphenoxy)-propoxy]-nitrobenzene in 75 ml of dimethylformamide and the reaction mixture is heated at 40° In the course of 15 minutes, 5.7 g of methyl iodide are added dropwise. The reaction mixture is then kept at 40° C. for a further one hour. After cooling, the mixture is poured onto dilute hydrochloric acid and extracted with methylene chloride and, by evaporation and recrystallisation from ether/hexane, 3-[3-(4-acetyl-3-methoxy-2-n-propylphenoxy)-propoxy]-nitrobenzene having a melting point of 52°–57° is obtained.

2.0 g of Raney nickel are added to a solution of 10 g of 3-[3-(4-acetyl-3-methoxy-2-n-propylphenoxy)-propoxy]-nitrobenzene in 100 ml of tetrahydrofuran and the whole is hydrogenated at room temperature. The catalyst is filtered off and washed with tetrahydrofuran. After concentration of the filtrate by evaporation under reduced pressure, 3-[3-(4-acetyl-3-methoxy-2-n-propylphenoxy)-propoxy]-aniline is obtained in the form of a colourless oil.

In the course of 10 minutes a solution of 3.45 ml of chloro-oxalic acid ethyl ester in 10 ml of methylene chloride is added dropwise to a solution of 9.2 g of 3-[3-(4-acetyl-3-methoxy-2-n-propylphenoxy)-propoxy]-aniline and 4.3 ml of triethanolamine in 90 ml of methylene chloride. After stirring for 5 hours at room temperature the mixture is poured onto water and extracted with methylene chloride. Concentration of the extracts by evaporation and recrystallisation of the residue from ether yields N-{3-[3-(4-acetyl-3-methoxy-2-n-propylphenoxy)-propoxy]-phenyl}-oxamic acid ethyl ester having a melting point of 91°–92°.

EXAMPLE 17

A spatula tip of potassium iodide and 3.2 g of N-[3-(3-bromopropoxy)-phenyl]-oxamic acid methyl ester are added to a suspension of 2.3 g of 2,4-dihydroxy-3-n-propylacetophenone and 1.6 g of calcined potassium carbonate in 40 ml of ethyl methyl ketone and the whole is heated under reflux for 8 hours. The reaction mixture is cooled, poured onto water and extracted three times with methylene chloride. The combined extracts are washed with water, dried over sodium sulphate and concentrated to dryness under reduced pressure. Crystallisation of the residue from ether yields N-{3-[3-(4-acetyl-3-hydroxy-2-n-propylphenoxy)-propoxy]-phenyl}-oxamic acid methyl ester having a melting point of 124°-125°.

The starting material can be manufactured as follows:

43 ml of 1,3-dibromopropane are added to a suspension of 29 g of potassium carbonate and 0.5 g of potassium iodide in 170 ml of acetone and the whole is heated under reflux. A solution of 19.4 g of 3-nitrophenol is then added dropwise thereto in the course of 2 hours and the whole is heated for a further 15 hours under reflux. The reaction mixture is filtered while hot and concentrated by evaporation. After chromatography of the residue over silica gel using toluene, 3-(3-bromopropoxy)-nitrobenzene is obtained in the form of a light yellow oil.

1 g of Raney nickel is added to a solution of 4 g of 3-(3-bromopropoxy)-nitrobenzene in 40 ml of tetrahydrofuran and the whole is hydrogenated at room temperature. The catalyst is filtered off and washed with tetrahydrofuran. After concentration of the filtrate by evaporation, 3-(3-bromopropoxy)-aniline is obtained in the form of a colourless oil.

A solution of 1.5 ml of oxalic acid monomethyl ester chloride in 10 ml of methylene chloride is added dropwise in the course of 10 minutes to a solution of 3.5 g of 3-(3-bromopropoxy)-aniline and 1.3 ml of pyridine in 40 ml of methylene chloride. After stirring for 2 hours at room temperature the mixture is poured onto water and extracted with methylene chloride. The combined extracts are concentrated by evaporation and the residue is chromatographed with methylene chloride/ethyl acetate (10:1) over silica gel. The eluate is concentrated by evaporation and the residue is crystallised from ether/hexane. N-[3-(3-bromopropoxy)-phenyl]-oxamic acid methyl ester having a melting point of 90°-91° is obtained.

EXAMPLE 18

A spatula tip of potassium iodide and 3.15 g of 4-(3-bromopropoxy)-2-hydroxy-3-propylacetophenone are added to a suspension of 1.8 g of N-(3-hydroxyphenyl)-oxamic acid methyl ester and 1.38 g of calcined potassium carbonate in 20 ml of ethyl methyl ketone and the whole is heated for 12 hours under reflux. The reaction mixture is cooled, poured onto water and extracted three times with methylene chloride. The combined extracts are washed with water, dried over sodium sulphate and concentrated to dryness under reduced pressure. Crystallisation of the residue from methylene chloride/ether yields N-{3-[3-(4-acetyl-3-hydroxy-2-n-propylphenoxy)-propoxy]-phenyl}-oxamic acid methyl ester having a melting point of 124°-125°.

The starting material is obtained, for example, as follows:

A solution of 1.9 ml of chloro-oxalic acid methyl ester in 10 ml of methylene chloride is added dropwise in the course of 10 minutes to a solution of 2.5 g of 3-aminoanisole and 1.5 ml of pyridine in 40 ml of methylene chloride. After stirring for 3 hours at room temperature the mixture is poured onto water and extracted with methylene chloride. The extracts are dried over sodium sulphate, concentrated by evaporation and crystallised from ether/hexane. N-(3-methoxyphenyl)-oxamic acid methyl ester is obtained.

5 g of boron tribromide are added dropwise in the course of 5 minutes to a solution, cooled to $-78°$ C., of 2 g of N-(3-methoxyphenyl)-oxamic acid methyl ester in 20 ml of methylene chloride. The whole is stirred for 5 hours at room temperature, 5 ml of water are added thereto while cooling and the organic phase is separated off. After drying over sodium sulphate and concentration by evaporation, N-(3-hydroxyphenyl)-oxamic acid methyl ester is obtained.

EXAMPLES 19

In a manner analogous to that described in Examples 1 to 18 there are also obtained:

N-{3-[3-(4-acetyl-3-hydroxy-2-n-propylphenoxy)-propoxy]-6-methylphenyl}-tetrazole-5-carboxamide and the sodium salt thereof having a melting point of 258°-260°;

N-{3-[3-(4-acetyl-3-hydroxy-2-n-propylphenoxy)-propoxy]-phenyl}-tetrazole-5-carboxamide and the sodium salt thereof;

N-{3-[3-(4-acetyl-3-hydroxy-2-n-propylphenoxy)-propoxy]-4-fluoro-6-methylphenyl}-tetrazole-5-carboxamide and the sodium salt thereof, N-{3-[3-(4-acetyl-3-hydroxy-2-n-propylphenoxy)-propoxy]-6-methylphenyl}-oxamic acid, melting point 178°-179°, and the triethanolammonium salt thereof;

N-{3-[3-(4-acetyl-3-hydroxy-2-n-propylphenoxy)-propoxy]-phenyl}-oxamic acid, melting point 159°-160°, and the triethanolammonium salt thereof;

N-{3-[3-(4-acetyl-3-hydroxy-2-propylphenoxy)-propoxy] -4-methoxycarbonylphenyl}-oxamic acid and the triethanolammonium salt thereof having a melting point of 99°-100°, and N-{3-[3-(4-acetyl-3-hydroxy-2-propylphenoxy)-propoxy]-4-carboxyphenyl}-oxamic acid and the mono- and di-sodium salts thereof.

EXAMPLE 20

Tablets containing 25 mg of active ingredient, for example the triethanolammonium salt of N-{3-[3-(4-acetyl-3-hydroxy-2-propylphenoxy)-propoxy]-6-methylphenyl}-oxamic acid, can be manufactured as follows:

| Constituents (for 1000 tablets): | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Preparation

All the solid ingredients are first forced through a sieve of 0.6 mm mesh width. Then the active ingredient, the lactose, the talc, the magnesium stearate and half the starch are mixed together. The other half of the starch is suspended in 40 ml of water and this suspension is added to a boiling solution of the polyethylene glycol in 100 ml of water and the mixture is granulated, if necessary with the addition of water. The granulate is dried overnight at 35°, forced through a sieve of 1.2 mm mesh width and compressed to form tablets of approximately 6 mm diameter that are concave on both sides.

Tablets containing 25 mg of another of the compounds of the formula I mentioned in Examples 1 to 19 can be manufactured in analogous manner, it being possible for compounds in which $R_2$ is carboxy or 5-tetrazolyl to be in the form of salts with bases, for example in the form of a sodium salt or a triethanolammonium salt, or in free form.

EXAMPLE 21

Tablets for chewing containing 30 mg of active ingredient, for example the triethanolammonium salt of N-{3-[3-(4-acetyl-3-hydroxy-2-propylphenoxy)-propoxy]-6-methylphenyl}-oxamic acid, can be manufactured, for example, as follows:

| Composition (for 1000 tablets) | |
|---|---|
| active ingredient | 30.0 g |
| mannitol | 267.0 g |
| lactose | 179.5 g |
| talc | 20.0 g |
| glycine | 12.5 g |
| stearic acid | 10.0 g |
| saccharine | 1.0 g |
| 5% gelatine solution | q.s. |

Preparation

All the solid ingredients are first forced through a sieve of 0.25 mm mesh width. The mannitol and the lactose are mixed, granulated with the addition of gelatine solution, forced through a sieve of 2 mm mesh width, dried at 50° and again forced through a sieve, of 1.7 mm mesh width. The active ingredient, the glycine and the saccharine are carefully mixed, the mannitol, the lactose granulate, the stearic acid and the talc are added and the whole is thoroughly mixed and compressed to form tablets of approximately 10 mm diameter that are concave on both sides and have a breaking groove on the upper side.

Tablets containing 30 mg of another of the compounds of the formula I mentioned in Examples 1 to 19 can be manufactured in analogous manner, it being possible for compounds in which $R_2$ is carboxy or 5-tetrazolyl to be in free form or in the form of salts with bases, for example in the form of a sodium salt or a triethanolammonium salt.

EXAMPLE 22

Tablets containing 100 mg of active ingredient, for example the triethanolammonium salt of N-{3-[3-(4-acetyl-3-hydroxy-2-propylphenoxy)-propoxy]-6-methylphenyl}-oxamic acid, can be manufactured as follows:

| Composition (for 1000 tablets): | |
|---|---|
| active ingredient | 100.0 g |
| lactose | 248.5 g |
| corn starch | 17.5 g |
| polyethylene glycol 6000 | 5.0 g |
| talc | 15.0 g |
| magnesium stearate | 4.0 g |
| demineralised water | q.s. |

Preparation

The solid ingredients are first forced through a sieve of 0.6 mm mesh width. Then the active ingredient, the lactose, the talc, the magnesium stearate and half the starch are intimately mixed. The other half of the starch is suspended in 65 ml of water and this suspension is added to a boiling solution of the polyethylene glycol in 260 ml of water. The resulting paste is added to the pulverulent substances and the whole is mixed and granulated, if necessary with the addition of water. The granulate is dried overnight at 35°, forced through a sieve of 1.2 mm mesh width and compressed to form tablets of approximately 10 mm diameter that are concave on both sides and have a breaking notch on the upper side.

Tablets containing 100 mg of a different compound of the formula I according to Examples 1 to 19 can also be manufactured in analogous manner, it being possible for compounds in which $R_2$ is carboxy or 5-tetrazolyl to be in free form or in the form of salts with bases, for example in the form of a sodium salt or a triethanolammonium salt.

EXAMPLE 23

A propellant-containing, solid aerosol-forming inhalation suspension containing 0.1% by weight of N-{3-[3-(4-acetyl-3-hydroxy-2-propylphenoxy)-propoxy]-6-methylphenyl}-oxamic acid (active ingredient) can be manufactured, for example, as follows:

| Composition | |
|---|---|
| active ingredient, micronised | 0.1% by weight |
| "sorbitan trioleate" | 0.5% by weight |
| propellant A (trichlorotrifluoroethane) | 4.4% by weight |
| propellant B (mixture of 15 parts of dichlorodifluoromethane and 80 parts of symmetrical dichlorotetrafluoroethane) | q.s. |

Preparation

In the absence of moisture, the active ingredient is suspended in the trichlorotrifluoroethane with the aid of a customary homogenising agent with the addition of the sorbitan trioleate, the suspension is introduced into a metering aerosol container, which is closed and filled under pressure with the dichlorodifluoromethane/dichlorotetrafluoroethane mixture.

Inhalation suspensions containing a different compound of the formula I according to Examples 1 to 19 can also be manufactured in analogous manner, it being possible for compounds in which $R_2$ is carboxy or 5-tetrazolyl to be in free form or in the form of salts with bases, for example in the form of a sodium salt or a triethanolammonium salt.

EXAMPLE 24

An approximately 2% aqueous solution (suitable for inhalation) of a triethanolammonium salt of N-{3-[3-(4-acetyl-3-hydroxy-2-propylphenoxy)-propoxy]-6-methylphenyl}-oxamic acid as active ingredient can be manufactured, for example, in the following composition:

| Composition | |
|---|---|
| active ingredient | 2000 mg |
| stabiliser, for example the disodium salt of ethylenediaminetetraacetic acid | 10 mg |
| preservative, for example benzalkonium chloride | 10 mg |
| water, freshly distilled | ad 100 ml |

Preparation

The active ingredient is dissolved in freshly distilled water. The stabiliser and the preservative are then added. When all the components have completely dissolved, the resulting solution is made up to 100 ml and introduced into small bottles, which are sealed in a gas-tight manner.

2% inhalation solutions containing a different active ingredient from one of Examples 1 to 19 can also be manufactured in analogous manner.

EXAMPLE 25

Capsules suitable for insufflation containing, for example, 25 mg of the triethanolammonium salt of N-{3-[3-(4-acetyl-3-hydroxy-2-propylphenoxy)-propoxy]-6-methylphenyl}-oxamic acid as active ingredient can be manufactured, for example, in the following composition:

| Composition | |
|---|---|
| active ingredient | 25 g |
| lactose, finely ground | 25 g |

Preparation

The active ingredient and the lactose are intimately mixed. The resulting powder is then sieved and introduced into 1000 gelatine capsules in portions of 50 mg.

Insufflation capsules each containing an active ingredient according to one of Examples 1 to 19 can also be manufactured in analogous manner.

We claim:

1. A 4-acyl resorcinol ether compound of the formula

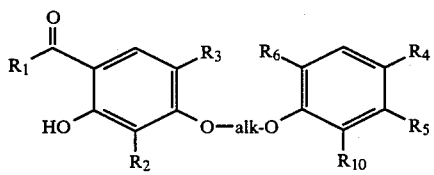

wherein
$R_1$ is lower alkyl;
$R_2$ is lower alkyl, lower alkenyl, or lower alkynyl;
$R_3$ is hydrogen, lower alkoxy, trifluoromethyl, or halogen;
alk is a lower alkylene radical;
one of $R_4$ and $R_5$ is $-\text{NHC(O)}-R_8$ and the other of $R_4$ and $R_5$ is $R_9$;
$R_6$ is hydrogen, lower alkyl, halogen, trifluoromethyl, carboxy, lower alkoxycarbonyl, carbamoyl, N-mono lower alkyl carbamoyl, N, N-di-lower alkyl carbamoyl, cyano, or lower alkanoyl;
$R_8$ is 5-tetrazolyl;
$R_9$ is hydrogen, lower alkyl, lower alkoxy, halogen, or trifluoromethyl; and
$R_{10}$ is hydrogen, lower alkyl, lower alkoxy, halogen, trifluoromethyl, cyano, carboxy, lower alkoxycarbonyl, carbamoyl, N-mono-lower alkyl carbamoyl, or N, N-di-lower alkyl carbamoyl;
wherein lower is up to and inclusive of 7 carbon atoms;
or a pharmaceutically acceptable salt thereof.

2. A compound of the formula

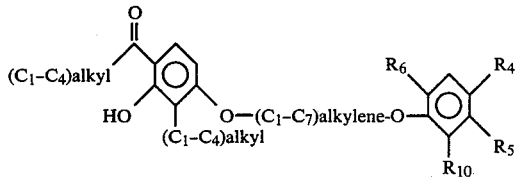

wherein
one of $R_4$ and $R_5$ is $-\text{NHC(O)}-R_8$ and the other is $R_9$;

$R_6$ is hydrogen, $(C_1-C_4)$alkyl, halogen having an atomic number of up to an including 35, cyano, $(C_1-C_4)$alkoxy-carbonyl, carboxy, or lower alkanoyl having up to and including 7 carbon atoms;
$R_8$ is 5-tetrazolyl;
$R_9$ is hydrogen, $(C_1-C_4)$alkyl, halogen having an atomic number from 17 to 53 inclusive, or trifluoromethyl; and
$R_{10}$ is hydrogen, $(C_1-C_4)$alkyl, $(C_1-C_4)$alkoxy, or halogen having an atomic number of up to an including 35;
or a pharmaceutically acceptable salt therof.

3. A compound according to claim 1 wherein $R_4$ denotes a group $R_9$, $R_5$ denotes a group of the formula $-\text{NH-C}(=\text{O})-R_8$ and the radical $R_1$, $R_2$, $R_3$, $R_6$, $R_8$, $R_9$ and $R_{10}$ having the meanings given in claim 1 or a pharmaceutically acceptable salt thereof.

4. A compound according to claim 1 in which $R_1$ represents lower alkyl having up to and including 4 carbon atoms, $R_2$ represents straight-chain lower alkyl having up to and including 4 carbon atoms, $R_3$ represents hydrogen, $R_4$ represents hydrogen, lower alkyl, trifluoromethyl, or halogen having an atomic number of up to and including 35, $R_5$ represents 5-tetrazolylcarbonylamino, $R_6$ represents hydrogen, lower alkyl having up to and including 4 carbon atoms, halogen having an atomic number of up to and including 35, lower alkoxycarbonyl having up to and including 5 carbon atoms, or carboxy, $R_{10}$ represents hydrogen, lower alkyl having up to and including 4 carbon atoms, halogen having an atomic number of up to and including 35, carboxy, lower alkoxycarbonyl having up to and including 5 carbon atoms, carbamoyl or cyano, and alk represents straight-chain, terminally bonded lower alkylene having up to and including 4 carbon atoms, or a pharmaceutically acceptable salt thereof, with a base.

5. A compound according to claim 1 in which $R_1$ represents lower alkyl having up to and including 4 carbon atoms, $R_2$ represents straight-chain lower alkyl having up to and including 4 carbon atoms, $R_3$ represents hydrogen, $R_4$ represents hydrogen, lower alkyl, trifluoromethyl, or halogen having an atomic number of up to and including 35, $R_5$ represents 5-tetrazolylcarbonylamino, $R_6$ represents hydrogen, lower alkyl having up to and including 4 carbon atoms, halogen having an atomic number of up to and including 5 carbon atoms, or carboxy, $R_{10}$ represents hydrogen, lower alkyl having up to and including 4 carbon atoms or halogen having an atomic number of up to and including 35, and alk represents straight-chain, terminally bonded lower alkylene having up to and including 4 carbon atoms, or a pharmaceutically acceptable salt thereof, with a base.

6. A compound according to claim 1 of the formula I, in which $R_1$ represents lower alkyl having up to and including 4 carbon atoms, $R_2$ represents straight-chain lower alkyl having up to and including 4 carbon atoms, $R_3$ and $R_{10}$ represent hydrogen, one of the radicals $R_4$ and $R_6$ represents lower alkyl having up to and including 4 carbon atoms, and the other represents halogen having an atomic number of up to an including 35, $R_5$ represents 5-tetrazolylcarbonylamino, and alk represents straight-chain, terminally bonded lower alkylene having up to and including 7 carbon atoms, or a pharmaceutically acceptable salt thereof, with a base.

7. A compound according to claim 1 of the formula

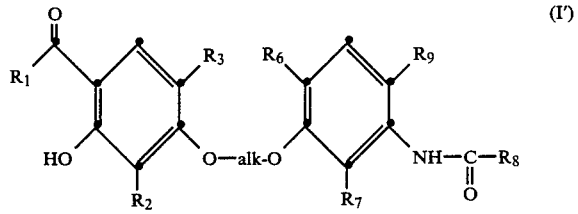

(I')

in which $R_1$ represents lower alkyl having up to and including 4 carbon atoms, $R_2$ represents lower alkyl having up to and including 4 carbon atoms, $R_3$ represents hydrogen, $R_6$ represents hydrogen, lower alkyl having up to and including 4 carbon atoms, halogen having an atomic number of up to and including 4 carbon atoms in the lower alkoxy moiety, carboxy, cyano or lower alkanoyl having up to and including 7 carbon atoms, $R_{10}$ represents hydrogen, lower alkyl having up to and including 4 carbon atoms, lower alkoxy having up to and including 4 carbon atoms, or halogen having an atomic number of up to and including 35, $R_8$ is 5-tetrazolyl, $R_9$ represents hydrogen, lower alkyl having up to and including 4 carbon atoms, halogen having an atomic number of from 17 up to and including 53, or trifluoromethyl, and alk represents lower alkylene having up to and including 4 carbon atoms, or a pharmaceutically acceptable salt thereof.

8. A compound according to claim 1 of the formula

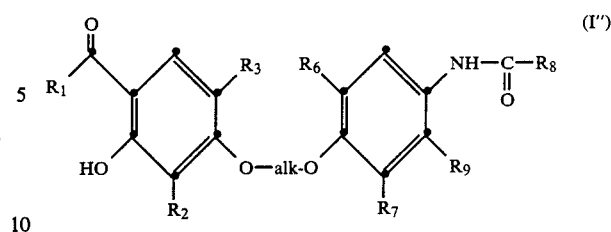

(I")

in which $R_1$ represents lower alkyl having up to and including 4 carbon atoms, $R_2$ represents lower alkyl having up to and including 4 carbon atoms, $R_3$ represents hydrogen, $R_6$ represents hydrogen, lower alkyl having up to and including 4 carbon atoms, halogen having an atomic number of up to and including 35, lower alkoxycarbonyl having up to and including 4 carbon atoms in the lower alkoxy moiety, carbonxy, or lower alkanoyl having up to and including 7 carbon atoms, $R_7$ is $R_{10}$ which represents hydrogen, lower alkyl having up to and including 4 carbon atoms, lower alkoxy having up to and including 4 carbon atoms, or halogen having an atomic number of up to and including 35, $R_8$ is 5-tetrazolyl, alk represents lower alkylene having up to and including 4 carbon atoms, provided that $R_3$, $R_6$, $R_9$ and $R_{10}$ are not all simultaneously hydrogen, or a pharmaceutically acceptable salt thereof.

9. A compound according to claim 1 of the formula

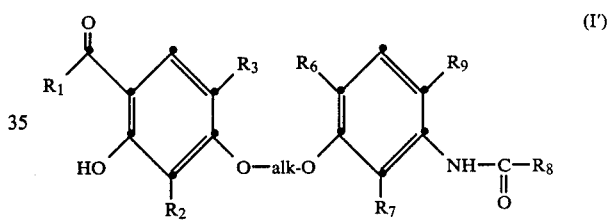

(I')

in which $R_1$ represents lower alkyl having up to and including 4 carbon atoms, $R_2$ represents straight-chain lower alkyl having up to and including 4 carbon atoms, $R_3$ represents hydrogen, $R_6$ represents hydrogen, lower alkyl having up to and including 4 carbon atoms, halogen having an atomic number of up to and including 35, lower alkoxycarbonyl having up to and including 5 carbon atoms, cyano or carboxy, $R_7$ is $R_{10}$ which represents hydrogen or lower alkyl having up to and including 4 carbon atoms or halogen having an atomic number of up to and including 35, $R_8$ represents 5-tetrazolyl, and alk represents straight-chain, terminally bonded lower alkylene having up to and including 7 carbon atoms, or a pharmaceutically acceptable salt thereof, with a base.

10. A compound as claimed in claim 1 being N- 3-[3-(4-acetyl-3-hydroxy-2-n-propylphenoxy)-propoxy]-4-bromo-6-methylphenyl -1H-tetrazole-5-carboxamide or a pharmaceutically acceptable salt thereof.

11. A compound as claimed in claim 1 being N- 3-[3-(4-acetyl-3-hydroxy-2-n-propylphenoxy)-propoxyl]-phenyl -1H-tetrazole-5-carboxamide or a pharmaceutically acceptable salt thereof.

12. A compound as claimed in claim 1 being N- 3-[3-(4-acetyl-3-hydroxy-2-n-propylphenoxy)-propoxy]-4-chloro-6-methylphenyl -1H-tetrazole-5-carboxamide or a pharmaceutically acceptable salt thereof.

13. A compound as claimed in claim 1 being N- 3-[3-(4-acetyl-3-hydroxy-2-n-propylphenoxy)-propoxy]-6- bromo-4-methylphenyl-1H-1, 2, 4-tetrazole-5-carboxamide or a pharmaceutically acceptable salt thereof.

14. The compound of claim 1 wherein
$R_1$ is lower alkyl having up to and including 4 carbon atoms;
$R_2$ is straight-chain $C_{2-4}$ alkyl;
$R_3$ is hydrogen;
$R_5$ is 5-tetrazolylcarbonylamino;
alk is an alpha, omega-bonded straight chain $C_{2-4}$ alkylene; and
(i) $R_4$ is hydrogen and $R_6$ and $R_7$ are each independently lower alkyl of up to and including 4 carbon atoms; or
(ii) $R_4$ is lower alkyl of up to and including 4 carbon atoms,
$R_6$ is hydrogen or halogen of atomic number up to and including 35, and $R_7$ is hydrogen; or
(iii) $R_4$, $R_6$, and $R_7$ are independently halogen of atomic number up to and including 35;
or the pharmaceutically acceptable salt thereof.

15. The compound of claim 12 which is N-[3-[3-(4-acethyl-3-hydroxy-2-n-propylphenoxy)-propoxyl]-4-chloro-6-methylphenyl]-1H-tetrazole-5-carboxamide triethylammonium salt.

16. A pharmaceutical anti-inflammatory or anti-allergic composition comprising a therapeutically effective amount of a compound of claim 1 and pharmaceutically acceptable carrier.

17. A method of treating an allergic or inflammatory condition in a mammal in need thereof comprising administering to said mammal a therapeutically effective amount of a compound of claim 1 or a pharmaceutically acceptable salt thereof.

18. A compound of claim 1 wherein $R_4$ is —NH-C(=O)-$R_8$, $R_5$ is $R_9$, and $R_1$, $R_2$, $R_3$, $R_6$, $R_9$, and $R_{10}$ are as defined in claim 1, or a pharmaceutically acceptable salt thereof except that $R_3$, $R_6$, $R_9$ and $R_{10}$ cannot all simultaneously be hydrogen.

19. A 4-acyl resorcinol ether compound of the formula

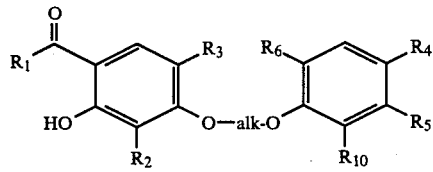

wherein
$R_1$ is lower alkyl;
$R_2$ is lower aklyl, lower alkenyl, or lwoer alkynyl;
$R_3$ is hydrogen, lower alkoxy, trifluoromethyl, or halogen;
alk is a lower alkylene radical;
one of $R_4$ and $R_5$ is —NHC(O)-$R_8$ and the other of $R_4$ and $R_5$ is $R_9$;
$R_6$ is hydrogen, lower alkyl, halogen, trifluoromethyl, carboxy, carbamoyl, N-mono lower alkyl carbamoyl, N, N-di-lower alkyl carbamoyl, or lower alkanoyl;
$R_8$ is carboxy;
$R_9$ is hydrogen, lower alkyl, lower alkoxy, halogen, or trifluoromethyl; and
$R_{10}$ is hydrogen, lower alkyl, lower alkoxy, halogen, trifluoromethyl, carboxy, carbamoyl, N-mono-lower alkyl carbamoyl, or N, N-di-lower alkyl carbamoyl; wherein lower is up to an inclusive of 7 carbon atoms; or a pharmaceutically acceptable salt thereof.

20. A compound of the formula

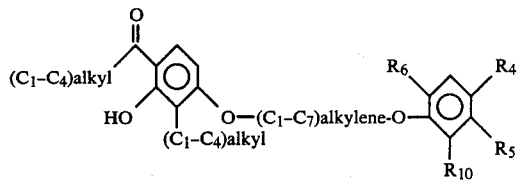

wherein
one of $R_4$ and $R_5$ is —NHC(O)-$R_8$ and the other is $R_9$;

$R_6$ is hydrogen, $(C_1-C_4)$alkyl, halogen having an atomic number of up to an including 35, carboxy, or lower alkanoyl having up to and including 7 carbon atoms;
$R_8$ is carboxy;
$R_9$ is hydrogen, $(C_1-C_4)$alkyl, halogen having an atomic number from 17 to 53 inclusive, or trifluoromethyl; and
$R_{10}$ is hydrogen, $(C_1-C_4)$alkyl, or halogen having an atomic number of up to and including 35;
or a pharmaceutically acceptable salt thereof.

21. A compound according to claim 19 wherein $R_4$ denotes a group $R_9$, $R_5$ denotes a group of the formula —NH-C(=O)-$R_8$ and the radicals, $R_1$, $R_2$, $R_3$, $R_6$, $R_8$, $R_9$ and $R_{10}$ having the meanings given in claim 45 or a pharmaceutically acceptable salt thereof.

22. A compound of claim 19 wherein $R_4$ is $R_9$, $R_5$ is —NH-C(=O)-$R_8$ and $R_1$, $R_2$, $R_3$, $R_6$, $R_8$, $R_9$, and $R_{10}$ are as defined in claim 44 or a pharmaceutically acceptable salt thereof except that $R_3$, $R_6$, and $R_9$ cannot all be hydrogen when $R_{10}$ is hydrogen, carboxy, or carbamoyl.

23. A compound according to claim 19, wherein $R_4$ denotes a group of the formula —NH-C(=O)-$R_8$, $R_5$ denotes a group $R_9$ and the radicals $R_1$, $R_2$, $R_3$, $R_6$, $R_9$ and $R_{10}$ having the meanings given in claim 45 or a pharmaceutically acceptable salt thereof.

24. A compound according to claim 19 in which $R_1$ represents lower alkyl having up to and including 4 carbon atoms, $R_2$ represents straight-chain lower alkyl having up to and including 4 carbon atoms, $R_3$ represents hydrogen, $R_4$ represents hydrogen, lower alkyl, trifluoromethyl, or halogen having an atomic number of up to and including 35, $R_5$ represents oxaloamino, $R_6$ represents hydrogen, lower alkyl having up to and including 4 carbon atoms, halogen having an atomic number of up to and including 35, or carboxy, $R_{10}$ represents hydrogen, lower alkyl having up to and including 4 carbon atoms, halogen having an atomic number of up to and including 35, carboxy, or carbamoyl, and alk represents straight-chain, terminally bonded lower alkylene having up to and including 4 carbon atoms, or a pharmaceutically acceptable salt thereof, with a base.

25. A compound according to claim 19 in which $R_1$ represents lower alkyl having up to and including 4 carbon atoms, $R_2$ represents straight-chain lower alkyl having up to and including 4 carbon atoms, $R_3$ represents hydrogen, $R_4$ represents hydrogen, lower alkyl, trifluoromethyl, or halogen having an atomic number of up to and including 35, $R_5$ represents oxaloamino, $R_6$ represents hydrogen, lower alkyl having up to and including 4 carbon atoms, halogen having an atomic number of up to and including 35, or carboxy, $R_{10}$ represent hydrogen, lower alkyl having up to and including 4 carbon atoms or halogen having an atomic number of up to and including 35, and alk represents straight-chain, terminally bonded lwoer alkylene having up to and including 4 carbon atoms, or a pharmaceutically acceptable salt thereof, with a base.

26. A compound according to claim 19 in which $R_1$ represents lower alkyl having up to and including 4 carbon atoms, $R_2$ represents straight-chain lower alkyl having up to and including 4 carbon atoms, $R_3$ and $R_{10}$ represent hydrogen, one of the radicals $R_4$ and $R_6$ represents lower alkyl having up to and including 4 carbon atoms, and the other represents halogen having an atomic number of up to and including 35, $R_5$ represents oxaloamino, ad alk represents straight-chain, terminally bonded lower alkylene having up to and including 7 carbon atoms, or a pharmaceutically acceptable salt thereof, with a base.

27. A compound according to claim 19 of the formula

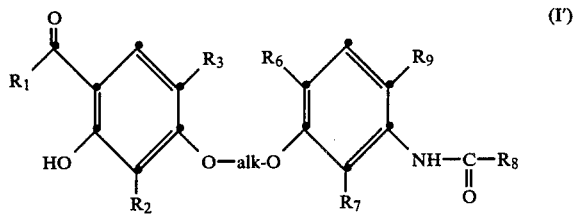

in which $R_1$ represents lower alkyl having up to and including 4 carbon atoms, $R_2$ represents lower alkyl having up to and including 4 carbon atoms, $R_3$ represents hydrogen, $R_6$ represents hydrogen, lower alkyl having up to and including 4 carbon atoms, halogen having an atomic number of up to and including 35, carboxy, or lower alkanoyl having up to and including 7 carbon atoms, $R_{10}$ represents hydrogen, lower alkyl having up to and including 4 carbon atoms, lower alkoxy having up to and including 4 carbon atoms, or halogen having an atomic number of or halogen having an atomic number of up to and including 35, $R_8$ represents carboxy, $R_9$ represents hydrogen, lower alkyl having up to and including 4 carbon atoms, halogen having an atomic number of from 17 up to and including 53, or trifluoromethyl, and alk represents lower alkylene having up to and including 4 carbon atoms, or a pharmaceutically acceptable salt thereof.

28. A compound according to claim 19 of the formula

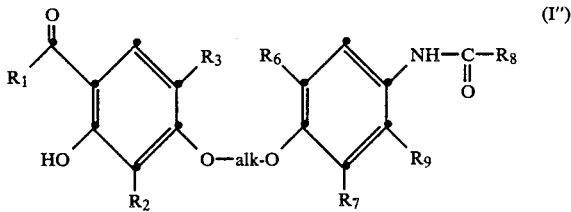

in which $R_1$ represents lower alkyl having up to and including 4 carbon atoms, $R_2$ represents lower alkyl having up to and including 4 carbon atoms, $R_3$ represents hydrogen, $R_6$ represents hydrogen, lower alkyl having up to and including 4 carbon atoms, halogen having an atomic number of up to and including 35, carboxy, or lower alkanoyl having up to and including 7 carbon atoms, $R_7$ is $R_{10}$ which represents hydrogen, lower alkyl having up to and including 4 carbon atoms, or halogen having an atomic number of up to and including 35, $R_8$ represents carboxy, alk represents lower alkylene having up to and including 4 carbon atoms.

29. A compound according to claim 19 of the formula

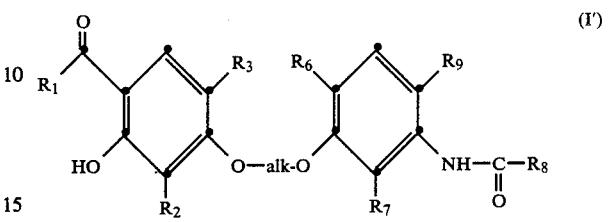

in which $R_1$ represents lower alkyl having up to and including 4 carbon atoms, $R_2$ represents straight-chain lower alkyl having up to and including 4 carbon atoms, $R_3$ represent hydrogen, $R_6$ represents hydrogen, lower alkyl having up to and including 4 carbon atoms, halogen having an atomic number of up to and including 35, or carboxy, $R_7$ is $R_{10}$ which represents hydrogen or lower alkyl having up to and including 4 carbon atoms or halogen having an atomic number of up to and including 35, $R_8$ represents carboxy, and alk represents straight-chain, terminally bonded lower alkylene having up to and including 7 carbon atoms, or a pharmaceutically acceptable salt thereof, with a base.

30. A compound as claimed in claim 19 being N-3-[3-(4-acetyl-3-hydroxy-2-n-propylphenoxy)-propoxyl]-4-bromo-6-methylphenyl-oxamic acid or a pharmaceutically acceptable salt thereof.

31. A compound as claimed in claim 19 being N-3-[3-(4-acetyl-3-hydroxy-2-n-propylphenoxy)-propoxyl]-6-chloro-4-methylphenyl -oxamic acid or a pharmaceutically acceptable salt thereof.

32. A compound as claimed in claim 19 being N-3-[3-(4-acetyl-3-hydroxy-2-n-propylphenoxy)-propoxyl]-4-chloro-6-methylphenyl -oxamic acid or a pharmaceutically acceptable salt thereof.

33. The compound of claim 19 wherein
   $R_1$ is lower alkyl having up to and including 4 carbon atoms;
   $R_2$ is straight-chain $C_{2-4}$ alkyl;
   $R_3$ is hydrogen;
   $R_5$ is oxaloamino;
   alk is an alpha, omega-bonded straight chain $C_{2-4}$ alkylene; and
   (i) $R_4$ is hydrogen and $R_6$ and $R_7$ are each independently lower aklyl of up to and including 4 carbon atoms; or
   (ii) $R_4$ is lower alkyl of up to and including 4 carbon atoms,
   $R_6$ is hydrogen or halogen of atomic number up to and including 35, and $R_7$ is hydrogen; or
   (iii) $R_4$, $R_6$, and $R_7$ are independently halogen of atomic number up to an including 35; or the pharmaceutically acceptable salt thereof.

34. A pharmaceutical anti-inflammatory or anti-allergic composition comprising a therapeutically effective amount of a compound of claim 19 and a pharmaceutically acceptable carrier.

35. A method of treating an allergic or inflammatory condition in a mammal in need thereof comprising administering to said mammal a therapeutically effective amount of compound of claim 19 or a pharmaceutically acceptable salt thereof.

* * * * *